US008778681B2

(12) United States Patent
Sano et al.

(10) Patent No.: US 8,778,681 B2

(45) Date of Patent: Jul. 15, 2014

(54) CULTURE METHOD RELATED TO DIFFERENTIATION OF PLURIPOTENT STEM CELLS INTO BLOOD CELLS

(71) Applicants: The University of Tokyo, Tokyo (JP); Terumo Kabushiki Kaisha, Tokyo (JP)

(72) Inventors: Shinya Sano, Kanagawa (JP); Koji Eto, Tokyo (JP); Naoya Takayama, Tokyo (JP); Hiromitsu Nakauchi, Tokyo (JP)

(73) Assignees: University of Tokyo, Tokyo (JP); Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/790,307

(22) Filed: Mar. 8, 2013

(65) Prior Publication Data

US 2013/0230882 A1 Sep. 5, 2013

Related U.S. Application Data

(63) Continuation of application No. PCT/JP2011/070563, filed on Sep. 9, 2011.

(30) Foreign Application Priority Data

Sep. 10, 2010 (JP) ................................ 2010-202752

(51) Int. Cl.
*C12N 5/00* (2006.01)

(52) U.S. Cl.
USPC ............................ 435/377; 435/325; 435/375

(58) Field of Classification Search
None
See application file for complete search history.

(56) References Cited

U.S. PATENT DOCUMENTS

| | | | |
|---|---|---|---|
| 2010/0197016 A1 | 8/2010 | Nakauchi et al. |
| 2011/0053267 A1 | 3/2011 | Nakauchi et al. |

FOREIGN PATENT DOCUMENTS

| | | |
|---|---|---|
| JP | 2003-125787 | 5/2003 |
| WO | 0029549 | 5/2000 |
| WO | 0029550 | 5/2000 |
| WO | 2008041370 | 4/2008 |
| WO | 2009122747 | 10/2009 |
| WO | 2010096746 | 8/2010 |
| WO | 2010099539 | 9/2010 |

OTHER PUBLICATIONS

Vodyanik et al. "Leukosialin (CD43) defines hematopoietic progenitors in human embryonic stem cell differentiation cultures." (2006) Blood, vol. 108: 2095-2105.*

Gabrilovich et al. "Vascular endothelial growth factor inhibits the development of dendritic cells and dramatically affects the differentiation of multiple hematopoietic lineages in vivo." (1998) Blood, vol. 92: 4150-4166.*

Eun Jung Baek, et al., Stroma-free mass production of clinical-grade red blood cells (RBCs) by using poloxamer 188 as an RBC survival enhancer, Transfusion, 49: 2285-2295, 2009.

Celine Bauwens, et al., Development of a Perfusion Fed Bioreactor for Embryonic Stem Cell-Derived Cardiomyocyte Generation: Oxygent-Mediated Enhancement of Cardiomyocyte Output, Biotechnology and Bioengineering, 90: 452-461, 2005.

Wolfgang Bergmeier, et al., Tumor Necrosis Factor-a-Converting Enzyme (ADAM17) Mediates GPIBa Shedding from Platelets in Vitro and In Vivo, Circulation Research, 95: 677-683, 2004.

E.E. Gardiner, et al., Controlled Shedding of platelet glycoprotein (GP)VI and GPIb-IX-V by ADAM family metalloproteinases, Journal of Thrombosis and Haemostasis, 5: 1530-1537, 2007.

Marion Kennedy, et al., Development of the hemangioblast defines the onset of hematopoiesis in human ES cell differentiation cultures, Blood, 109: 2679-2687, 2007.

Helene Lapillonne, et al., Red blood cell generation from human induced pluripotent stem cells: perspectives for transfusion medicine, Haematologica, 95(10): 1651-1659, 2010.

Shi-Jiang Lu, et al., Biological properties and enucleation of red blood cells from human embryonic stem cells, Blood, 112: 4475-4484, 2008.

Feng Ma, et al., Generation of functional erythrocytes from human embryonic stem cell-derived definitive hematopoiesis, Proceedings of the National Academy of Sciences, 105: 13087-13092, 2008.

Nimet Maherali, et al., Directly Reprogrammed Fibroblasts Show Global Epigenetic Remodeling and Widespread Tissue Contribution, Cell Stem Cell 1: 55-70, 2007.

Enca Martin-Rendon, et al., Transcriptional Profiling of Human Cord Blood CD133+ and Cultured Bone Marrow Mesenchymal Stem Cells in Response to Hypoxia, Stem Cells, 25: 1003-1012, 2007.

Kenichi Miharada, et al., Efficient enucleation of erythroblasts differentiated in vitro from hematopoietic stem and progenitor cells, Nature Biotechnology, 24: 1255-1256, 2006.

Sigma Mostafa, et al., Oxygen tension influences the differentiation, maturation and apoptosis of human megakaryocytes, British Journal of Haematology, 111: 879-889, 2000.

Masato Nakagawa, et al., Generation of induced pluripotent stem cells without Myc from mouse and human fibroblasts, Nature Biotechnology, 26: 101-106, 2008.

Keisuke Okita, et al., Generation of germline-competent induced pluripotent stem cells, Nature 448:313-317, 2007.

In-Hyun Park, et al., Reprogramming of human somatic cells to pluripotency with defined factors, Nature 451: 141-146, 2007.

Sonia Prado-Lopez, et al., Hypoxia Promotes Efficient Differentiation of Human Embryonic Stem Cells to Functional Endothelium, Stem Cells, 28: 407-418, 2010.

Caihong Qiu, et al., Globin switches in yolk sac-like primitive and fetal-like definitive red blood cells produced from human embryonic stem cells, Blood, 111: 2400-2408, 2008.

(Continued)

*Primary Examiner* — Jon P Weber
*Assistant Examiner* — Teresa E Knight
(74) *Attorney, Agent, or Firm* — Pearne & Gordon LLP

(57) ABSTRACT

It is an object of the present invention to provide a method for efficient differentiation into blood cells. Specifically, in the present invention, when blood cells are produced from pluripotent stem cells such as ES cells or iPS cells in vitro, the cells are cultured under a low oxygen partial pressure to increase the efficiency of differentiating the pluripotent stem cells into hematopoietic progenitor cells, erythroid progenitor cells, and the like, so as to increase the number of finally obtained, desired blood cells.

29 Claims, 11 Drawing Sheets

(56) References Cited

OTHER PUBLICATIONS

Shinya Sano, et al., Development of a method for Hematopoietic Differentiation and Culture of Human Pluripotent Stem Cells Utilizing Oxigen Condition Change, Regenerative Medicine, 10: 151, 2011.
Matthias Stadtfield, et al., Induced Pluripotent Stem Cells Generated Without Viral Integration, Science 322: 945-949, 2008.
Kazutoshi Takahashi, et al., Induction of Pluripotent Stem Cells from Mouse Embryonic and Adult Fibroblast Cultures by Defined Factors, Cell 126: 663-676, 2006.
Kazutoshi Takahashi, et al., Induction of Pluripotent Stem Cells from Adult Human Fibroblasts by Defined Factors, Cell, 131: 861-872, 2007.
Naoya Takayama, et al. Generation of functional platelets from human embryonic stem cells in vitro via ES-sacs, VEGF-promoted structures that concentrate hematopoietic progenitors, Blood, 111: 5298-5306, 2008.
Marius Wernig, et al., In vitro reprogramming of fibroblasts into a pluripotent ES-cell-like state, Nature 448: 318-324, 2007.
Marius Wernig, et al., c-Myc Is Dispensable for Direct Reprogramming of Mouse Fibroblasts, Cell Stem Cell, 2: 10-12, 2008.
Junying Yu, et al., Induced Pluripotent Stem Cell Lines Derived from Human Somatic Cells, Science, 318: 1917-1920, 2007.
International Search Report dated Nov. 29, 2011 for corresponding application PCT/JP2011/070563.
European Search Report for PCT/JP2011/070563 dated Feb. 25, 2014, Apr. 3, 2014.
Notice of Rejection dated Apr. 22, 2014 for Japanese Patent Application No. 2012-533036.

* cited by examiner

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial
<220> FEATURE:
<223> OTHER INFORMATION: Synthetic nucleotides

<400> SEQUENCE: 1

gctgtgacag gtacccaacc                                      20


<210> SEQ ID NO 2
<211> LENGTH: 21
<212> TYPE: DNA
<213> ORGANISM: Artificial
<220> FEATURE:
<223> OTHER INFORMATION: Synthetic nucleotides

<400> SEQUENCE: 2

catgcaggtg agttgtcaga a                                    21


<210> SEQ ID NO 3
<211> LENGTH: 26
<212> TYPE: DNA
<213> ORGANISM: Artificial
<220> FEATURE:
<223> OTHER INFORMATION: Synthetic nucleotides

<400> SEQUENCE: 3

ctatgagatg gagattactg atggtc                               26


<210> SEQ ID NO 4
<211> LENGTH: 18
<212> TYPE: DNA
<213> ORGANISM: Artificial
<220> FEATURE:
<223> OTHER INFORMATION: Synthetic nucleotides
```

<400> SEQUENCE: 4
gtgtggggat cagcttgc 18

<210> SEQ ID NO 5
<211> LENGTH: 22
<212> TYPE: DNA
<213> ORGANISM: Artificial
<220> FEATURE:
<223> OTHER INFORMATION: Synthetic nucleotides

<400> SEQUENCE: 5
gaacatttgg gaaatctctt gc 22

<210> SEQ ID NO 6
<211> LENGTH: 23
<212> TYPE: DNA
<213> ORGANISM: Artificial
<220> FEATURE:
<223> OTHER INFORMATION: Synthetic nucleotides

<400> SEQUENCE: 6
cggaagaaca atgtagtctt tgc 23

<210> SEQ ID NO 7
<211> LENGTH: 21
<212> TYPE: DNA
<213> ORGANISM: Artificial
<220> FEATURE:
<223> OTHER INFORMATION: Synthetic nucleotides

<400> SEQUENCE: 7
gtgaaattga ctcagggcat c 21

<210> SEQ ID NO 8
<211> LENGTH: 21
<212> TYPE: DNA
<213> ORGANISM: Artificial
<220> FEATURE:
<223> OTHER INFORMATION: Synthetic nucleotides

<400> SEQUENCE: 8
cccctgtcct tcttaaactc c 21

<210> SEQ ID NO 9
<211> LENGTH: 20
<212> TYPE: DNA
<213> ORGANISM: Artificial
<220> FEATURE:
<223> OTHER INFORMATION: Synthetic nucleotides

<400> SEQUENCE: 9
ccttgctgct ctacctccac 20

<210> SEQ ID NO 10
<211> LENGTH: 20
<212> TYPE: DNA
<213> ORGANISM: Artificial
<220> FEATURE:
<223> OTHER INFORMATION: Synthetic nucleotides

<400> SEQUENCE: 10
ccacttcgtg atgattctgc 20

<210> SEQ ID NO 11

<211> LENGTH: 21
<212> TYPE: DNA
<213> ORGANISM: Artificial
<220> FEATURE:
<223> OTHER INFORMATION: Synthetic nucleotides

<400> SEQUENCE: 11
ttggaggact tggtgtgttt c 21

<210> SEQ ID NO 12
<211> LENGTH: 19
<212> TYPE: DNA
<213> ORGANISM: Artificial
<220> FEATURE:
<223> OTHER INFORMATION: Synthetic nucleotides

<400> SEQUENCE: 12
agcttccatg gctcatcct 19

<210> SEQ ID NO 13
<211> LENGTH: 19
<212> TYPE: DNA
<213> ORGANISM: Artificial
<220> FEATURE:
<223> OTHER INFORMATION: Synthetic nucleotides

<400> SEQUENCE: 13
gagacaccca tgtgcagga 19

<210> SEQ ID NO 14
<211> LENGTH: 18
<212> TYPE: DNA
<213> ORGANISM: Artificial
<220> FEATURE:
<223> OTHER INFORMATION: Synthetic nucleotides

<400> SEQUENCE: 14
agctggggca cacatacg 18

<210> SEQ ID NO 15
<211> LENGTH: 21
<212> TYPE: DNA
<213> ORGANISM: Artificial
<220> FEATURE:
<223> OTHER INFORMATION: Synthetic nucleotides

<400> SEQUENCE: 15
gacacatatg cagccactcc t 21

<210> SEQ ID NO 16
<211> LENGTH: 20
<212> TYPE: DNA
<213> ORGANISM: Artificial
<220> FEATURE:
<223> OTHER INFORMATION: Synthetic nucleotides

<400> SEQUENCE: 16
atgatgggca agttgtaccc 20

<210> SEQ ID NO 17
<211> LENGTH: 25
<212> TYPE: DNA
<213> ORGANISM: Artificial
<220> FEATURE:
<223> OTHER INFORMATION: Synthetic nucleotides

<400> SEQUENCE: 17

```
gacatgaagt tcacctactg tgatg                                        25


<210> SEQ ID NO 18
<211> LENGTH: 21
<212> TYPE: DNA
<213> ORGANISM: Artificial
<220> FEATURE:
<223> OTHER INFORMATION: Synthetic nucleotides

<400> SEQUENCE: 18

gcgcatggta gaattcatag g                                            21


<210> SEQ ID NO 19
<211> LENGTH: 21
<212> TYPE: DNA
<213> ORGANISM: Artificial
<220> FEATURE:
<223> OTHER INFORMATION: Synthetic nucleotides

<400> SEQUENCE: 19

aacagcctca agatcatcag c                                            21


<210> SEQ ID NO 20
<211> LENGTH: 21
<212> TYPE: DNA
<213> ORGANISM: Artificial
<220> FEATURE:
<223> OTHER INFORMATION: Synthetic nucleotides

<400> SEQUENCE: 20

ttggcaggtt tttctagacg g                                            21
```

CULTURE METHOD RELATED TO DIFFERENTIATION OF PLURIPOTENT STEM CELLS INTO BLOOD CELLS

RELATED APPLICATIONS

This patent application is a continuation of international patent application No. PCT/JP2011/070563 filed on Sep. 9, 2011, which claims priority from Japanese patent application No. 2010-202752, filed Sep. 10, 2010, which are both incorporated herein by reference in their entireties.

REFERENCE TO A SEQUENCE LISTING, A TABLE, OR A COMPUTER PROGRAM LISTING APPENDIX SUBMITTED AS AN ASCII TEXT FILE

The material in the ASCII text file, named WING2-50480-SeqListing.txt, created Mar. 8, 2013, file size 4096 bytes, is hereby incorporated by reference.

TECHNICAL FIELD

The present invention relates to a cell culture method for differentiating cells into blood cells. More specifically, the present invention relates to a cell culture method comprising differentiating cells capable of differentiating into hematopoietic progenitor cells into the hematopoietic progenitor cells and further differentiating the hematopoietic progenitor cells into blood cells.

BACKGROUND ART

A stable supply of various types of blood cells in necessary amounts is extremely important for the treatment of blood-related diseases. To date, various types of blood cells have been mainly produced from blood collected from donors, and the thus produced blood cells have been used for treatments such as surgery. However, due to the chronic shortage of donors, it has not been easy to promptly secure sufficient amounts of blood cells when needed. In particular, platelets that are cells essential for blood coagulation (hemostasis) are essential for leukemia, bone marrow transplantation, anticancer therapy and like. However, since platelets collected from donors cannot be preserved in a frozen state, there is a high need for an effective means for stably supplying such platelets.

Recently, attempts have been vigorously made to produce various types of blood cells from pluripotent stem cells such as ES cells or iPS cells in vitro, without depending on the blood donation, and the practical use thereof has gained attention. For example, Takayama et al. have reported that they have succeeded in generation of platelets from human ES cells (Patent Literature 1 and Non Patent Literature 1). In addition, it has been disclosed that platelets can be produced also from iPS cells (Patent Literature 2).

As a result of the development of a method for producing blood cells from pluripotent stem cells in vitro, a majority of various types of blood cells, which will be used in medical sites in the future, would be produced from pluripotent stem cells. Thus, it is anticipated that the chronic shortage of blood cells could be overcome. However, the current situation is that only small amounts of blood cells can be produced by the previously reported methods for producing blood cells from iPS cells or ES cells, it is difficult to secure blood cells in amounts necessary for treatments such as surgery. Accordingly, in order to promote the differentiation of iPS cells or ES cells into blood cells by a certain method, it is necessary to improve conventional methods.

When cell differentiation is induced, an oxygen concentration is different between in vivo induction and in vitro induction. Several reports showed that progenitor cells were cultured in an oxygen concentration lower than an atmospheric oxygen environment and differentiated into various kinds of cells in vitro. (Non Patent Literature 2 to Non Patent Literature 5, and Patent Literature 3 to Patent Literature 5). For example, the following methods have been reported so far: a method of culturing cells capable of differentiating into cartilage under low oxygen conditions, so as to carry out cartilage differentiation (Patent Literature 3); a method of culturing undifferentiated central nervous system cells (Patent Literature 4) or neural crest stem cells (Patent Literature 5) under low oxygen conditions; a method of culturing ES cells in a low oxygen concentration and then culturing them in an atmospheric oxygen concentration, so as to differentiate the cells into cardiac muscle cells (Non Patent Literature 5); and the like. However, there have not yet been detailed reports regarding the influence of a low oxygen concentration on the differentiation of cells into blood cells.

CITATION LIST

Patent Literature

Patent Literature 1: WO 2008/041370

Patent Literature 2: WO 2009/122747

Patent Literature 3: JP Patent Publication (Kokai) No. 2003-125787 A

Patent Literature 4: WO00/29550

Patent Literature 5: WO00/29549

Non Patent Literature

Non Patent Literature 1: Takayama et al., Blood, 111: 5298-5306, 2008

Non Patent Literature 2: Kennedy et al., Blood, 109: 2679-2687, 2007

Non Patent Literature 3: Prado-Lopez et al., Stem Cells, 28: 407-418, 2010

Non Patent Literature 4: Martin-Rendon et al., Stem Cells, 25: 1003-1012, 2010

Non Patent Literature 5: Bauwens et al., Biotechnol Bioeng., 90: 452-461, 2005

SUMMARY OF INVENTION

Technical Problem

The present inventors had already obtained hematopoietic progenitor cells from pluripotent stem cells, and they had further established a method for differentiating the obtained hematopoietic progenitor cells into various types of blood cells. However, the amounts of blood cells produced by this method are small, and thus, it is not sufficient as amounts used for treatment and the like.

Hence, taking into consideration such circumstances, the present invention is directed towards establishing a method for stably producing large amounts of blood cells in vitro. That is, it is an object of the present invention to provide: a novel method for inducing differentiation into hematopoietic progenitor cells; and hematopoietic progenitor cells produced by the above-mentioned method, and various types of blood cells induced to be differentiated from the hematopoietic progenitor cells.

Solution to Problem

In a step of inducing the differentiation of pluripotent stem cells into hematopoietic progenitor cells, the present inventors have cultured the cells under a low oxygen partial pressure (also means oxygen concentration, oxygen tension or oxygen gas condition) for a certain period of time. As a result, the inventors have found that the number of the induced hematopoietic progenitor cells becomes greater than that in the case of carrying out the cell culture only under an atmospheric oxygen partial pressure, thereby completing the present invention.

Specifically, the present invention relates to the following (1) to (16).

(1) A method for producing hematopoietic progenitor cells or erythroid progenitor cells, which comprises a step of culturing cells capable of differentiating into hematopoietic progenitor cells or erythroid progenitor cells under an environment in which an oxygen partial pressure increases.

(2) The method for producing hematopoietic progenitor cells or erythroid progenitor cells according to (1) above, wherein the environment in which an oxygen partial pressure increases is an environment comprising a step of culturing cells under a low oxygen partial pressure.

(3) The method for producing hematopoietic progenitor cells or erythroid progenitor cells according to (2) above, wherein the low oxygen partial pressure is 0.1% to 10%.

(4) The method for producing hematopoietic progenitor cells or erythroid progenitor cells according to (2) or (3) above, which is characterized in that when the cells are cultured under the low oxygen partial pressure, a hypoxia-responsive gene is expressed at a higher level than that in a case in which the cells are cultured under other partial pressures.

(5) The method for producing hematopoietic progenitor cells or erythroid progenitor cells according to any one of (2) to (4) above, wherein the cells are cultured under the low oxygen partial pressure for a certain period of time after the beginning of the cell culture, and thereafter, the cells are further cultured under a higher oxygen partial pressure.

(6) The method for producing hematopoietic progenitor cells or erythroid progenitor cells according to (5) above, wherein the certain period of time is 4 to 10 days.

(7) The method for producing hematopoietic progenitor cells or erythroid progenitor cells according to (5) or (6) above, wherein the certain period of time is a period of time until $KDR^{+}$, $CD34^{+}$ or $CD43^{+}$ cells appear.

(8) The method for producing hematopoietic progenitor cells or erythroid progenitor cells according to any one of (5) to (7) above, which is characterized in that the time at which the low oxygen partial pressure is changed to a higher oxygen partial pressure is the time at which a gene used as an indicator of mesendoderm induction is expressed, the time at which the expression of a gene used as an indicator of hematopoietic progenitor cell induction begins, the time at which the expression of a gene used as an indicator of differential proliferative cytokine begins, or the time at which the expression of a gene used as an indicator of blood cell induction begins.

(9) The method for producing hematopoietic progenitor cells or erythroid progenitor cells according to any one of (5) to (8) above, wherein the higher oxygen partial pressure is an oxygen partial pressure of 11% to 30%.

(10) The method for producing hematopoietic progenitor cells or erythroid progenitor cells according to any one of (1) to (9) above, wherein the cells capable of differentiating into hematopoietic progenitor cells or erythroid progenitor cells are pluripotent stem cells.

(11) The method for producing hematopoietic progenitor cells or erythroid progenitor cells according to any one of (1) to (10) above, which is characterized in that the hematopoietic progenitor cells or erythroid progenitor cells are obtained from a sac-like structure or an embryoid.

(12) The method for producing hematopoietic progenitor cells or erythroid progenitor cells according to any one of (1) to (11) above, which is characterized in that VEGF is not added to a medium in which the cell culture is carried out.

(13) Hematopoietic progenitor cells or erythroid progenitor cells produced by the method according to any one of (1) to (12) above.

(14) Blood cells produced by further culturing the hematopoietic progenitor cells or erythroid progenitor cells according to (13) above.

(15) A pharmaceutical preparation comprising the blood cells according to (14) above.

(16) A method for screening for a substance that promotes or inhibits differentiation into hematopoietic progenitor cells or erythroid progenitor cells, wherein the screening method is characterized in that it uses the production method according to (1) above.

Advantageous Effects of Invention

According to the present invention, it becomes possible to increase the numbers of hematopoietic progenitor cells, erythroid progenitor cells, and blood cells, which are produced by induction of cell differentiation, in comparison with a conventional method.

According to the present invention, it becomes possible to reduce a culture period necessary for obtaining a desired number of hematopoietic progenitor cells, erythroid progenitor cells, or blood cells.

According to the present invention, hematopoietic progenitor cells can be produced without using VEGF that has been conventionally necessary for efficient induction of the hematopoietic progenitor cells.

According to the present invention, hematopoietic progenitor cells and erythroid progenitor cells having a high potential to differentiate into blood can be obtained.

BRIEF DESCRIPTION OF DRAWINGS

In FIGS. 6A and 6B, erythrocytes were examined In FIG. 6C, megakaryocytic cells were examined, and in FIG. 6D, platelets were examined It is to be noted that FIG. 6A indicates the number of blood cells derived from ES cells (KhES-3) and FIGS. 6B to 6D indicate the number of blood cells derived from iPS cells (TkCB7-2). In each figure, (1) indicates the results of a culture performed under an oxygen partial pressure of 21% for 14 days and then carrying out a culture for differentiation into erythrocytes, and (2) indicates the results of a culture performed under an oxygen partial pressure of 5% for 7 days and then under an oxygen partial pressure of 21% for 7 days, followed by a culture for differentiation into erythrocytes.

FIG. 7A shows the percentage of β globin-positive cells in erythrocytes derived from ES cells (KhES-3), and FIG. 7B shows the percentage of β globin-positive cells in erythrocytes derived from iPS cells (TkCB7-2). In each figure, (1) indicates the results of a culture performed under an oxygen partial pressure of 21% for 14 days and then carrying out a culture for differentiation into erythrocytes, and (2) indicates the results of a culture performed under an oxygen partial pressure of 5% for 7 days and then under an oxygen partial pressure of 21% for 7 days, followed by a culture for differentiation into erythrocytes. In addition, FIG. 7C shows the results obtained by double-staining erythrocytes with DAPI and, an anti-human hemoglobin antibody (left view) or an anti-human β globin antibody (right view).

FIG. 8A shows the results obtained by counting the number of blood cells generated after completion of the culture, and FIG. 8B shows the results of flow cytometry performed on the cells generated after completion of the culture. In each figure, (1) indicates the results of a culture performed in the presence of VEGF under an oxygen partial pressure of 21% for 14 days, and (2) indicates the results of a culture performed in the absence of VEGF under an oxygen partial pressure of 5% for 7 days and then under an oxygen partial pressure of 21% for 7 days. In the experiments, iPS cells (cell line: TkCB7-4) were used.

FIG. 9A shows the results obtained using iPS cells (cell line: TkCB7-4), FIG. 9B shows the result obtained using iPS cells (cell line: TkCB8-3), and FIG. 9C shows the results using ES cells (cell line: KhES3). In each figure, (1) indicates the results of a culture performed in the presence of VEGF under an oxygen partial pressure of 21% for 14 days, and (2) indicates the results of a culture performed in the absence of VEGF under an oxygen partial pressure of 5% for 7 days and then under an oxygen partial pressure of 21% for 7 days. The symbols “n,” “m,” “E,” “M” and “blast” indicate neutrophil, macrophage, erythroblast, megakaryocyte and hematopoietic blast cells, respectively. A combination of such letters means that the cells corresponding to individual letters are mixed (for example, “nm” means that neutrophils are present together with macrophages). The longitudinal axis in FIG. 9A indicates the number of colonies derived from $5\times10^3$ blood cells. The longitudinal axis in FIG. 9B indicates the number of colonies derived from $1\times10^4$ blood cells. The longitudinal axis in FIG. 9C indicates the number of colonies derived from $1\times10^5$ ES cells. The number that is close to each bar in the graph indicates the number of mixed colonies.

FIG. 12A shows an experiment performed under an oxygen partial pressure of 5%, and FIG. 12B shows an experiment performed under an oxygen partial pressure of 1%. The longitudinal axis indicates a relative value of a total number of blood cells, when N- is defined as 1. The symbols "L4-," "L7-," and "L10-" indicate the results obtained by changing a low oxygen environment to an oxygen partial pressure of 21% on the $4^{th}$, $7^{th}$, and $10^{th}$ days after the beginning of the culture, respectively. In addition, on "L14," a low oxygen culture was entirely carried out. On "N—," a culture was entirely carried out under an oxygen partial pressure of 21%. In all of the cultures, VEGF was not added.

DESCRIPTION OF EMBODIMENTS

Figure 1:
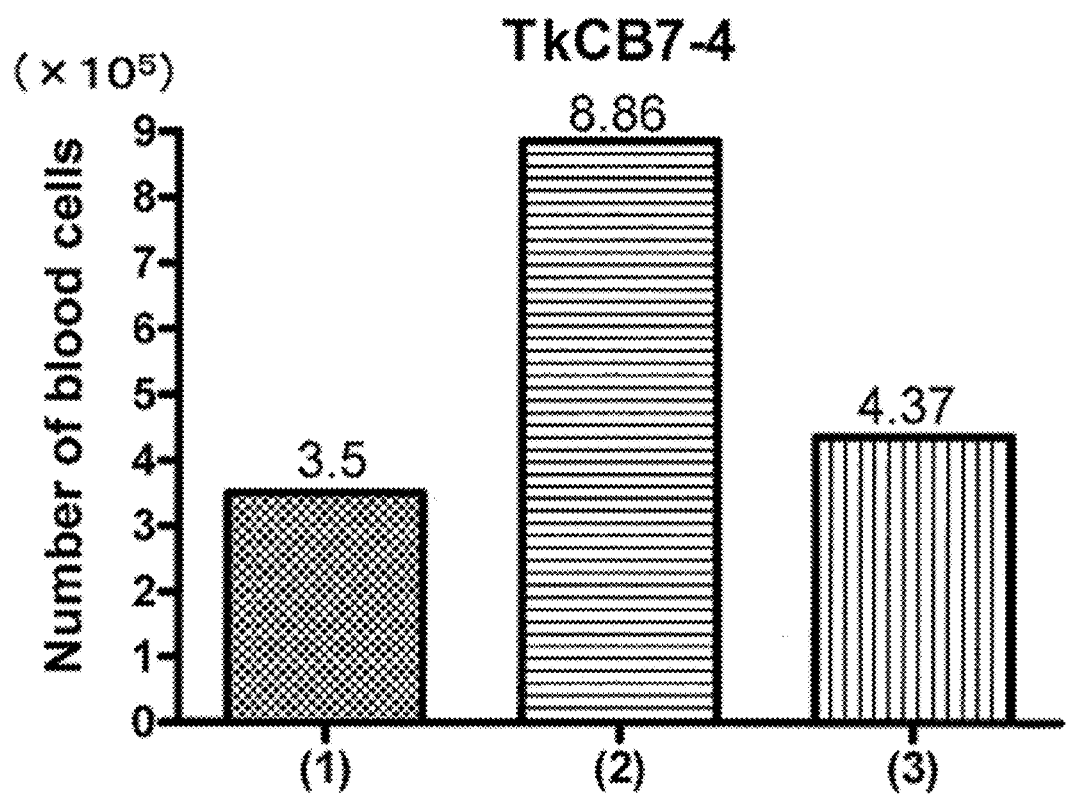
FIG. 1 shows the effects of a culture performed under a low oxygen partial pressure on differentiation into blood cells. The longitudinal axis indicates the number of blood cells generated after completion of the culture. In the figure, (1) indicates the results of a culture performed under an oxygen partial pressure of 21% for 14 days; (2) indicates the results of a culture performed under an oxygen partial pressure of 5% for 7 days and then under an oxygen partial pressure of 21% for 7 days; and (3) indicates the results of a culture performed under an oxygen partial pressure of 5% for 14 days. The experiments (1), (2), and (3) were all carried out in the presence of 20 ng/ml VEGF. In the experiments, iPS cells (cell line: TkCB7-4) were used.

One embodiment of the present invention is: a method for differentiating cells that are capable of differentiating into hematopoietic progenitor cells or erythroid progenitor cells, into hematopoietic progenitor cells or erythroid progenitor cells, which comprises a step of culturing the cells capable of differentiating into hematopoietic progenitor cells or erythroid progenitor cells under an environment in which an oxygen partial pressure increases; or a method for producing hematopoietic progenitor cells or erythroid progenitor cells, which comprises a step of culturing cells capable of differentiating into hematopoietic progenitor cells or erythroid progenitor cells under a low oxygen partial pressure.

In addition, another embodiment of the present invention is: a method for differentiating cells that are capable of differentiating into hematopoietic progenitor cells or erythroid progenitor cells, which comprises a step of culturing the cells capable of differentiating into hematopoietic progenitor cells or erythroid progenitor cells under a low oxygen partial pressure; or a method for producing hematopoietic progenitor cells or erythroid progenitor cells, which comprises a step of culturing cells capable of differentiating into hematopoietic progenitor cells or erythroid progenitor cells under a low oxygen partial pressure.

Herein, the types of the "cells capable of differentiating into hematopoietic progenitor cells or erythroid progenitor cells" are not particularly limited. Examples of such cells include pluripotent stem cells (ES cells, iPS cells, etc.). Or, any types of cells may be used, as long as they are at a differentiation stage between pluripotent stem cells and hematopoietic progenitor cells. Preferably, ES cells or iPS cells are used.

The ES cells used in the present invention are not particularly limited. In general, ES cells can be obtained by repeating an operation to culture a fertilized egg at a blastocyst stage together with feeder cells, to disintegrate proliferating inner cell mass-derived cells, and then to subculture them, so as to be finally established as an ES cell line. Thus, ES cells are obtained from a fertilized egg. In addition to these ES cells, there may also be used ES cell-like cells, which are obtained from cells or tissues other than fertilized eggs, such as fat tissues, chorionic villus, amniotic fluid, placenta or testicular cells, have characteristics similar to those of ES cells, and also have pluripotent differentiation ability.

In addition, the iPS cells used in the present invention are not particularly limited. Cells of all origins may be used as iPS cells, as long as they have achieved pluripotent differentiation ability equivalent to that of ES cells as a result of introducing several types of transcription factor (hereinafter referred to as "pluripotent differentiation factor" in this description) genes imparting pluripotent differentiation ability into somatic cells (e.g. fibroblasts, blood cells, etc.). As such pluripotent differentiation factors, many factors have already been reported. Examples of such a pluripotent differentiation factor include, but are not limited to, Oct family (e.g. Oct3/4), SOX family (e.g. SOX2, SOX1, SOX3, SOX15, SOX17, etc.), Klf family (e.g. K1f4, K1f2, etc.), MYC family (e.g. c-MYC, N-MYC, L-MYC, etc.), NANOG, and LIN28. Regarding a method for establishing iPS cells, a large number of publications have been published. Such publications can be referred to (see, for example, Takahashi et al., Cell 2006, 126: 663-676; Okita et al., Nature 2007, 448: 313-317; Wernig et al., Nature 2007, 448: 318-324; Maherali et al., Cell Stem Cell 2007, 1: 55-70; Park et al., Nature 2007, 451: 141-146; Nakagawa et al., Nat Biotechnol 2008, 26: 101-106; Wernig et al., Cell Stem Cell 2008, 10: 10-12; Yu et al., Science 2007, 318: 1917-1920; Takahashi et al., Cell 2007, 131: 861-872; Stadtfeld et al., Science 2008 322: 945-949).

The hematopoietic progenitor cells differentiated or produced by the present invention mean hematopoietic cells, which are characterized by a single maker or a combination of multiple markers selected from among $CD34^-$ (CD34-negative), $CD34^+$ (CD34-positive), $Lin^-$ (CD2, CD3, CD4, CD7, CD8, CD10, CD14, CD16, CD19, CD20, CD24, CD41, CD45, CD56, CD66b, or CD235a-negative), $CD38^-$ (CD38-negative), $CD90^+$ (CD90-positive), $CD49f^+$ (CD49f-positive), $VEGFR2^+$ (VEGFR2-positive), $CD31^+$ (CD31-positive), $CD43^+$ (CD43-positive), $CD34^+/CD45^+$ (CD34-positive and CD45-positive), Rhodamine-weakly-positive, and Hoechst-negative/weakly positive. Moreover, the erythroid progenitor cells differentiated or produced by the present invention mean hematopoietic cells, which are characterized as $CD71^+$ (CD71-positive), GPA (Glycophorin A)$^+$ (GPA-positive), $GPA^+/CD41^+$ (GPA-positive/CD41-positive), or GPA (Glycophorin A)$^+/CD45^+$ (GPA-positive/CD45-positive). Furthermore, megakaryocytes and platelets differentiated or produced by the present invention mean hematopoietic cells, which are characterized as $CD41^+$ (CD41-positive), $CD42b^+$ (GPA-positive), $CD41^+/CD42b^+$ (CD41-positive/CD42b-positive), or $GPA^-/CD41^+$ (GPA-negative/CD41-positive).

The animal, from which the "cells" used in the present invention are derived, is a human or a non-human animal (e.g. mouse, rat, bovine, horse, swine, sheep, monkey, dog, cat, bird, etc.), and thus, it is not particularly limited. A human is particularly preferable.

In the present invention, among cell culture conditions for inducing differentiation into hematopoietic progenitor cells or erythroid progenitor cells, conditions other than an oxygen partial pressure condition may be selected, as appropriate, by a person skilled in the art. For example, when ES cells or iPS cells are used as "cells capable of differentiating into hematopoietic progenitor cells or erythroid progenitor cells," conditions, in which a sac-like structure or an embryoid can be formed in the process of inducing the differentiation of the ES cells or iPS cells into hematopoietic progenitor cells or erythroid progenitor cells, can be used as cell culture conditions.

The term "sac-like structure" prepared from ES cells or iPS cells is used herein to mean a three-dimensional sac-like (having a space inside) structure derived from ES cells or iPS cells, which is formed from an endothelial cell population or the like, and which contains hematopoietic progenitor cells and erythroid progenitor cells therein. For the details of the sac-like structure, please see TAKAYAMA et al., BLOOD 2008, 111: 5298-5306, for example.

Culture conditions in which a sac-like structure is formed from ES cells or iPS cells are different depending on the types of ES cells or iPS cells used. For example, as a medium, there can be used IMDM, to which FBS (final concentration: 15%) has been added. Further, even in the case of a serum-free culture, a medium, to which a growth factor, a supplement and the like have been added as appropriate, can be used. In conventional methods, a culture is carried out with addition of VEGF (0 to 100 ng/ml, and more preferably, approximately 20 ng/ml), in order to efficiently form a sac-like structure. When a culture is carried out under a low oxygen environment, as disclosed in the present invention, even if VEGF is not added, effects equivalent to the case of adding VEGF can be obtained. Culture conditions other than the oxygen partial pressure are different depending on the types of ES cells or iPS cells used. For example, conditions consisting of 5% $CO_2$, and a temperature of 36° C. to 38° C., preferably of 37° C., can be applied. The culture period until formation of the sac-like structure is different depending on the types of ES cells or iPS cells used. The culture period is generally about 14 to 16 days, after the cells have been plated on feeder cells. The formed sac-like structure has a follicular structure, and inside the structure, hematopoietic progenitor cells and erythroid progenitor cells are present in a condensed state. The hematopoietic progenitor cells and erythroid progenitor cells that are present inside the sac-like structure can be separated by physical means, for example, by allowing the sac-like structure to pass through a sterilized sieving device (e.g. a cell strainer). The thus obtained hematopoietic progenitor cells or erythroid progenitor cells are further cultured, so as to differentiate them into various types of blood cells.

Moreover, as conditions for culturing hematopoietic progenitor cells or erythroid progenitor cells from ES cells or iPS cells (which are conditions other than the oxygen partial pressure), there can be used conditions in which a cell mass called embryoid that contains differentiated cells of endoderm, mesoderm and ectoderm can be formed. Such conditions are different depending on the types of ES cells or iPS cells used. For example, IMDM comprising FBS (final concentration: 15%), transferrin and the like, to which a growth factor, a supplement and the like have been further added as appropriate, can be used as a medium. Moreover, the culture environment other than the oxygen partial pressure is different depending on the types of ES cells or iPS cells used. For example, conditions consisting of 5% $CO_2$, and a temperature of 36° C. to 38° C., preferably of 37° C., can be applied.

In the present invention, the phrase "environment in which an oxygen partial pressure increases" is used to mean an environment comprising conditions for increasing the oxygen partial pressure during a culture. This environment may be an artificially produced environment. The phrase "an oxygen partial pressure increases" is used herein to mean that the oxygen partial pressure may increase in a low oxygen partial pressure range or it may also increase in a higher oxygen partial pressure range. Alternatively, the oxygen partial pressure may increase in a range in which a low oxygen partial pressure is shifted to a higher oxygen partial pressure. Even if it is an environment in which the oxygen partial pressure fluctuates up and down during a culture, if it is an environment in which the oxygen partial pressure temporarily increases, such an environment is included in the "environment in which an oxygen partial pressure increases" of the present invention.

The phrase "low oxygen partial pressure" is used in the present invention to mean an oxygen partial pressure of, for example, 0.1% to 10%, preferably 1% to 5%, and more preferably approximately 5%, of oxygen gas by volume of a total volume of the gas to which the cell culture is subjected. Otherwise, an oxygen partial pressure, under which a hypoxia-responsive gene can be expressed, may be selected as a "low oxygen partial pressure." Herein, examples of such a hypoxia-responsive gene include HIFα, HIF1α, HIF3α, HIF1β, GLUT-1, p21, p57, FoxO, Notch1, VEGF, ABCG2/Bcrp-1, CXCR4, PDK-1, c-Kit, and other related genes.

The term "expression" is used in the present invention to mean that a gene is transcribed and mRNA is synthesized, that the mRNA of a gene is translated into a protein, or that the protein of a gene exhibits its functions.

During a cell culture that is carried out for induction of the differentiation of, or production of, hematopoietic progenitor cells from cells capable of differentiating into the hematopoietic progenitor cells, all of the steps may be carried out under a low oxygen partial pressure. However, it is preferable that the cell culture is carried out under a low oxygen partial pressure until the appearance of hematopoietic progenitor cells exhibiting, for example, $KDR^+$, $CD34^+$ and $CD43^+$, and then that the cells be cultured under a higher oxygen partial pressure, for example, under an atmospheric oxygen partial pressure of 21%. For example, when a culture is carried out under conditions for forming a sac-like structure from human ES cells or human iPS cells, it is preferable that the culture be carried out under a low oxygen partial pressure (e.g. an oxygen partial pressure of approximately 5%) for 1 to 10 days, preferably for 4 to 8 days, and more preferably for approximately 7 days after the beginning of the culture of the ES cells or iPS cells, and then that the cells be cultured under a higher oxygen partial pressure.

Otherwise, the timing of shifting the oxygen partial pressure from a low oxygen partial pressure to a higher oxygen partial pressure may be determined using a change in the expression of a specific gene as an indicator. The type of such a specific gene is not particularly limited. Examples of the specific gene include a gene used as an indicator of mesendoderm induction, a gene used as an indicator of hematopoietic progenitor cell induction, a gene used as an indicator of differential proliferative cytokine, and a gene used as an indicator of blood cell induction. It is desired to shift the oxygen partial pressure from a low oxygen partial pressure to an atmospheric oxygen partial pressure around the timing at which, for example, a gene used as an indicator of mesendoderm induction is expressed. On the other hand, in the case of using a gene used as an indicator of hematopoietic progenitor cell induction, a gene used as an indicator of differential proliferative cytokine, and a gene used as an indicator of blood cell induction, it is desired to shift the oxygen partial pressure from a low oxygen partial pressure to an atmospheric oxygen partial pressure, until around the beginning of the expression of each gene.

Examples of the above-described gene used as an indicator of mesendoderm induction include T, SOX-17, GATA-4, HNF-3β, GSC, Cer1, Nodal, FGF8, Mix11, FGF4 CD48, DKK4, FGF17, GATA-6, CXCR4, c-Kit, CD99, OTX2, and Nodal. Examples of the above-described gene used as an indicator of hematopoietic progenitor cell induction include TAL-1, KDR, CD34, CXCR4, c-Kit, RUNX-1, GATA-1, GATA-2, CD43, ETV-2, Tie-2, CD31, CLOUDIN5, and Sca-1. Examples of the above-described gene used as an indicator of differential proliferative cytokine include VEGF, EPOR, EPO, TPO, BMP4, FGF-2, FLT-1, Ang-1, SDF-1, and SCF. Examples of the above-described gene used as an indicator of blood cell induction include CD41, Glycophorin-A, c-MPL, Rh antigen, α4 integrin, KLF-1, BCL-11A, CD45, β-Globin, α-Globin, ε-Globin, and γ-Globin.

The phrase "a higher oxygen partial pressure" is used herein to mean an oxygen partial pressure higher than the oxygen partial pressure applied at the beginning of the culture of cells capable of differentiating into hematopoietic progenitor cells (low oxygen partial pressure). The higher oxygen partial pressure is an oxygen partial pressure of, for example, approximately 11% to 30%, and more preferably approximately 15% to 25%. The "higher oxygen partial pressure" is particularly preferably an atmospheric oxygen partial pressure of approximately 21%.

Another embodiment of the present invention is a method for inducing the differentiation of, or producing various types of blood cells, which comprises further culturing the hematopoietic progenitor cells or erythroid progenitor cells produced by the method of the present invention.

A large number of methods for inducing the differentiation of hematopoietic progenitor cells or erythroid progenitor cells into various types of blood cells have been known in the present technical field (for example, Miharada et al., Nat Biotechnol 2006, 24: 1255-1256; Qiu et al., Blood 2008, 111: 2400-2408; Ma et al., PNAS 2008, 105: 13087-13092; Lu et al., Blood 2008, 112: 4475-4484; Baek et al., Transfusion 2009, 11: 2285-2295; Lapillonne et al., haematologica 2010, doi: 10. 3324). Accordingly, a person skilled in the art could readily select such a differentiation induction method and carry out it.

For example, when mature megakaryocytic cells, and further, platelets are produced from the hematopoietic progenitor cells produced by the method of the present invention, conditions in which any one of, or a combination of two or more of TPO, IL-1α, IL-3, IL-4, IL-5, IL-6, IL-9, IL-11, EPO, GM-CSF, SCF, G-CSF, Flt3 ligand, Heparin and the like have been added to the cells, may be used as culture conditions. More specifically, examples of the conditions for inducing the differentiation of the cells into mature megakaryocytic cells and platelets include conditions in which the cells are cultured, for example, in the presence of TPO (10 to 200 ng/mL, and preferably approximately 100 ng/mL), or in the presence of TPO (10 to 200 ng/mL, and preferably approximately 100 ng/mL), SCF (10 to 200 ng/mL, and preferably approximately 50 ng/mL) and Heparin (10 to 100 U/mL, and preferably approximately 25 U/ml), for approximately 7 to 15 days. The culture environment is not particularly limited, as long as it is an environment suitable for induction of the differentiation of blood cells in vitro. For instance, the culture may be carried out under conditions consisting of 5% $CO_2$, and a temperature of 36° C. to 38° C., preferably of 37° C.

Examples of conditions for suitable for inducing the differentiation of the erythroid progenitor cells produced by the method of the present invention into mature erythrocytes include conditions in which any one of, or a combination of two or more of TPO, IL-α, IL-3, IL-4, IL-5, IL-6, IL-9, IL-11, EPO, GM-CSF, SCF, G-CSF, Flt3 ligand, IGF-I, IGF-II, Dexamethasone, Hydrocortisone, Mifepristone, Heparin and the like have been added to the cells. More specifically, examples of the conditions for inducing the differentiation of the cells into erythrocytes include conditions in which the cells are cultured, for example, in the presence of EPO (2 to 100 U/mL, and preferably approximately 10 U/mL), or in the presence of EPO (2 to 100 U/mL, and preferably approximately 10 U/mL), SCF (10 to 200 ng/mL, and preferably approximately 50 ng/mL) and TPO (5 to 200 ng/mL, and preferably approximately 20 ng/ml), for approximately 7 to 25 days. The culture environment is not particularly limited, as long as it is an environment suitable for induction of the differentiation of blood cells in vitro. For instance, the culture may be carried out under conditions consisting of 5% $CO_2$, and a temperature of 36° C. to 38° C., preferably of 37° C.

Various types of blood cells produced by the present invention can be stably supplied in the form of blood preparations. When the method of the present invention is applied to produce, for example, platelets and the produced platelets are then processed into a platelet preparation, a fraction of a culture solution in which platelets are abundant is recovered, and thereafter, blood cell components other than platelets, such as megakaryocytic cells, are removed using a leukocyte reduction filter or the like, so as to prepare a platelet preparation. Upon preparation of such blood preparations, it is possible to allow the blood preparations to comprise other components useful for stabilization of platelets or erythrocytes. As such components useful for stabilization, those well known to experts in the present technical field can be selected.

More specifically, the obtained platelets can be processed into a platelet preparation according to the following method.

An ACD-A solution and FFP (fresh frozen plasma prepared from whole blood obtained by blood donation, wherein FFP comprises all components other than blood components, such as albumin and a coagulation factor) are added at a ratio of 1:10 to the obtained platelets, and the thus obtained mixture is then exposed to 15-50 Gy of radiation. Thereafter, while stirring the resultant at 20° C. to 24° C., it is preserved. The ACD-A solution is prepared by adding water for injection to 22 g of sodium citrate/8 g of citric acid/22 g of glucose, resulting in a total volume of 1 L.

When the above-described method is applied, the platelet level is desirably set at approximately $1\times10^9$ platelets/mL, for example.

If GM 6001 (a broad-range hydroxamic acid-based metalloprotease inhibitor) (Calbiochem, La Jolla, Calif., USA) has been added to the platelets, inactivation of the platelets associated with the cleavage of platelet functional molecules such as GPIb-V-1× and GPVI, which occurs during frozen storage and storage at room temperature, can be prevented. The present inventors have confirmed that inactivation of mouse ES cell-derived platelets can be prevented by this method. As for reference documents regarding platelet inactivation mechanism using human platelets, please refer to Bergmeier, W et al., Cir Res 95: 677-683, 2004, and Gardiner, E E et al., J Thrombosis and Haemostasis, 5: 1530-1537, 2007.

It is preferable to avoid the use of a material for activating platelets, such as glass, as a vessel for storing a preparation containing platelets.

In addition, when the present invention is used to produce, for example, erythrocytes and the produced erythrocytes are then processed into an erythrocyte preparation, the production method can be carried out as follows.

A MAP solution (the composition of which is as described below) is added to a concentrated erythrocyte solution prepared by centrifuging a culture supernatant and then concentrating the resultant. Thereafter, the obtained mixture is exposed to 15-50 Gy of radiation, and it is then preserved at 2° C. to 6° C.

When the above-described method is applied, the erythrocyte level is desirably set at approximately $1\times10^{10}$ erythrocytes/mL, for example. For the obtained erythrocytes, there can be used an additive solution for erythrocyte preservation (MAP solution), which is prepared by dissolving, for example, D-mannitol (14.57 g), adenine (0.14 g), crystalline sodium dihydrogen phosphate (0.94 g), sodium citrate (1.50 g), citric acid (0.20 g), glucose (7.21 g) and sodium chloride (4.97 g) in water for injection to a total amount of 1000 ml.

A person skilled in the art could readily select other known methods suitable for production of erythrocyte preparations, as appropriate.

A further embodiment of the present invention is a method for screening for a substance that promotes or inhibits differentiation into hematopoietic progenitor cells or erythroid progenitor cells, wherein the screening method is characterized in that it uses the differentiation method or the production method of hematopoietic progenitor cells or erythroid progenitor cells of the present invention. Specifically, in a step of culturing cells that is carried out in the method of the present invention, a candidate differentiation-promoting substance or a candidate differentiation-inhibiting substance is added into a medium at an appropriate timing, for an appropriate period of time, and the number of the obtained hematopoietic progenitor cells or erythroid progenitor cells is then counted. Thereafter, the obtained results are compared with those from an experiment performed as a control (wherein the same culture step is carried out without adding a candidate substance), and the effects of the promoting substance or inhibiting substance can be then evaluated. If the number of hematopoietic progenitor cells or erythroid progenitor cells obtained from the experiment using the substance is larger than the number of the cells obtained from the control experiment, the candidate substance can be evaluated as a differentiation-promoting substance. In contrast, the aforementioned number is smaller than the number obtained from the control experiment, the candidate substance can be evaluated as a differentiation-inhibiting substance.

Hereinafter, the present invention will be described more in detail in the following examples. However, these examples are used to only illustrate several embodiments of the present invention, and are not intended to limit the scope of the present invention.

EXAMPLES

<Materials and Methods>

1. Cells and Reagents

As human iPS cells, TkCB7-2, TkCB7-4, and TkCB8-3 that had been established by introduction of four Yamanaka factors (OCT3/4, KLF4, SOX2, and c-MYC) were used. For the maintenance culture of such iPS cells, there was used a medium prepared by adding 0.1 mM non-essential amino acid (Invitrogen), 2 mM L-glutamine (Invitrogen), 20% knockout serum replacement (Invitrogen), 0.1 mM 2-mercaptoethanol (SIGMA), and 5 ng/mL basic fibroblast growth factor (bFGF; Upstate) to a Dulbecco modified Eagle medium and Ham F-12 medium (SIGMA). The iPS cells were cultured on irradiated (50 Gy) mouse embryonic fibroblasts (MEF), and the cells were then subcultured every three days, so that they could be maintained in an undifferentiated state. At the same time, mouse $C_3H_{10}T1/2$ cells used as feeder cells were cultured on Eagle basal medium (Invitrogen), to which 10% fetal bovine serum (FBS) and 2 mM L-glutamine had been added.

As a differentiation medium, there was used Iscove modified Dulbecco medium (SIGMA), to which 10 μg/mL human insulin, 5.5 μg/mL human transferrin, 5 ng/mL sodium selenite (SIGMA), 2 mM L-glutamine, 0.45 mM α-monothioglycerol (SIGMA), 50 μg/mL ascorbic acid (SIGMA), and 15% highly filtered FBS (Cellect Gold; ICN Biomedicals) had been added. To the thus prepared differentiation medium, a human vascular endothelial cell growth factor (R & D Systems) was added or was not added.

The above-described culture was carried out at 37° C. under 5% $CO_2$, using a $CO_2$ incubator HERA CELL 150i (Thermo SCIENTIFIC).

In addition, as ES cells, a KhES3 cell line was used. These cells were also subjected to maintenance culture and differentiation under the same conditions as those for iPS cells.

2. Production of iPS Cell- or ES Cell-derived Sac-like Structure (Hereinafter Referred to as iPS-Sac or ES-Sac)

A culture step for preparing a sac-like structure, which was carried out in the present example, will be described below (For the details thereof, please refer to TAKAYAMA et al., BLOOD 2008, 111: 5298-5306).

Previously, irradiated (50 Gy) $C_3H_{10}T1/2$ cells had been placed on a 100-mm dish, and human iPS cells or ES cells ($1\times10^5$ each) had been then plated on a differentiation medium. Thereafter, the cells were cultured in a $CO_2$ incubator, into which nitrogen gas had been injected to set the oxygen concentration to an atmospheric oxygen concentration (21% $O_2$) or to a low oxygen concentration (5% or 1% $O_2$), while the culture period had been selected, as appropriate, from a period between 1 and 14 days. Thereafter, the cells, which were cultured in a low oxygen concentration, were transferred to atmospheric oxygen conditions, or were continuously cultured. The culture was carried out for total 14 days, so as to produce iPS-Sac or ES-Sac.

3. Recovery of Blood Cells from iPS-Sac or ES-Sac

The iPS-Sac or ES-Sac was peeled from the dish and was then disintegrated. The resultant was suspended in PBS that contained 3% FBS, and the suspension was then passed through a 40-μm cell strainer (BD). The passed solution was centrifuged at 440×g for 10 minutes, so as to recover blood cells. Thereafter, the number of cells was counted.

4. Flow Cytometric Analysis

The expression of a cell surface antigen was analyzed by flow cytometry (MoFlo, Beckman Coulter). The cells were stained with a phycoerythrin (PE)-conjugated-anti-CD34 antibody, a phycoerythrin (PE)-conjugated-anti-CD42b antibody, an Alexa405-conjugated-anti-CD45 antibody, an allophycocyanin (APC)-conjugated-anti-glycophorin A antibody, and an allophycocyanin (APC)-conjugated-anti-CD41a antibody (BD Biosciences).

5. Colony Assay of Hematopoietic Progenitor Cells (HPCs)

HPCs (5-10×$10^3$) recovered from iPS-Sac or ES-Sac was suspended in Metho Cult GF H4434 (Stem Cell Technologies), to which 50 ng/ml thrombopoietin (R & D Systems) had been added, and the obtained suspension was then plated on a 35-mm dish. Thereafter, the cells were cultured in a $CO_2$ incubator for 13-14 days, and the generated colonies were then picked up. The obtained colonies were centrifuged at 800 rpm for 1 minute, using Shandon Cytospin 4 (Thermo SCIENTIFIC), and they were then stained with Hemacolor Rapid staining of blood smear (MERCK), followed by observation.

6. Immunostaining of Mature Erythrocytes

HPCs recovered from iPS-Sac or ES-Sac was differentiated into mature erythrocytes, and the mature erythrocytes were then centrifuged using Shandon Cytospin 4. Thereafter, the resultant was attached to a slide glass. This resultant was fixed with 4% paraformaldehyde, and was then permeabilized in 0.1% TritonX-100, followed by blocking with skim milk. As primary antibodies, an anti-human hemoglobin antibody (Bethyl Laboratories) and an anti-human β globin antibody (Santa Cruz Biotechnology) were allowed to react with the erythrocytes, and the resultant cells were then stained with an Alexa488-conjugated-anti-goat antibody and an Alexa546-conjugated-anti-mouse antibody (Invitrogen) used as secondary antibodies. The obtained cells were enclosed with VECTASHIELD Mounting Medium with DAPI (Vector Laboratories), and were then observed under a confocal scanning microscope FV1000 (Olympus). The percentage of β globin-positive cells was calculated using the formula: (the number of β globin-positive cells/the number of hemoglobin-positive cells)×100.

7. Gene Expression Analysis by Real-time PCR iPS-Sac or ES-Sac was treated using RNeasy Mini Kit (QIAGEN), so that total RNA was purified. The RNA was reversely transcribed to cDNA, and it was then analyzed with 7900HT Fast Real-Time PCR System (Applied Biosystems), using Roche Universal Probe (Roche Applied Science). Glyceraldehyde-3-phosphate dehydrogenase (GAPDH) was used as an internal standard gene.

The primer sequences of individual genes T, TAL-1, KDR, CD34, VEGF, EPOR, CD41a, Glycophorin-A, HIF2α and GAPDH are shown below.

```
                                        (SEQ ID NO: 1)
T:              forward; gctgtgacaggtacccaacc

                                        (SEQ ID NO: 2)
T:              reverse; catgcaggtgagttgtcagaa

                                        (SEQ ID NO: 3)
TAL-1:          forward; ctatgagatggagattactgatggtc

                                        (SEQ ID NO: 4)
TAL-1:          reverse; gtgtggggatcagcttgc

                                        (SEQ ID NO: 5)
KDR:            forward; gaacatttgggaaatctcttgc

                                        (SEQ ID NO: 6)
KDR:            reverse; cggaagaacaatgtagtctttgc

                                        (SEQ ID NO: 7)
CD34:           forward; gtgaaattgactcagggcatc

                                        (SEQ ID NO: 8)
CD34:           reverse; cccctgtccttcttaaactcc

                                        (SEQ ID NO: 9)
VEGF:           forward; ccttgctgctctacctccac

                                        (SEQ ID NO: 10)
VEGF:           reverse; ccacttcgtgatgattctgc

                                        (SEQ ID NO: 11)
EPOR:           forward; ttggaggacttggtgtgtttc

                                        (SEQ ID NO: 12)
EPOR:           reverse; agcttccatggctcatcct

                                        (SEQ ID NO: 13)
CD41a:          forward; gagacacccatgtgcagga

                                        (SEQ ID NO: 14)
CD41a:          reverse; agctggggcacacatacg

                                        (SEQ ID NO: 15)
Glycophorin-    forward; gacacatatgcagccactcct
A:

                                        (SEQ ID NO: 16)
Glycophorin-    reverse; atgatgggcaagttgtaccc
A:

                                        (SEQ ID NO: 17)
HIF2α:          forward; gacatgaagttcacctactgtgatg

                                        (SEQ ID NO: 18)
HIF2α:          reverse; gcgcatggtagaattcatagg

                                        (SEQ ID NO: 19)
GAPDH:          forward; aacagcctcaagatcatcagc

                                        (SEQ ID NO: 20)
GAPDH:          reverse; ttggcaggtttttctagacgg
```

<Results>

1. Effects of Low Oxygen Culture on Differentiation of iPS Cells into Blood Cells iPS cells (TkCB7-4) were plated on a differentiation medium. Thereafter, the cells were cultured under an atmospheric oxygen partial pressure (21%) for 14 days (FIG. 1 (1)), or the cells were cultured under a low oxygen partial pressure (5%) for 7 days and then under an atmospheric oxygen partial pressure (21%) for 7 days (FIG. 1(2)), or the cells were cultured under a low oxygen partial pressure (5%) for 14 days (FIG. 1 (3)). Subsequently, the number of blood cells generated in an iPS-Sac was counted in each of the above-mentioned three cases. As a result, the number of blood cells generated was highest in the case in which the cells were cultured under a low oxygen partial pressure for 7 days and then under an atmospheric oxygen partial pressure for 7 days (FIG. 1 (2)). From these results, it was found that the number of blood cells can be increased by beginning the culture of iPS cells under a low oxygen partial pressure so that the cells can be cultured under such a low oxygen partial pressure for a certain period of time.

2. Effects of Low Oxygen Culture on Differentiation of iPS Cells into Hematopoietic Progenitor Cells (HPCs)

Figure 2:
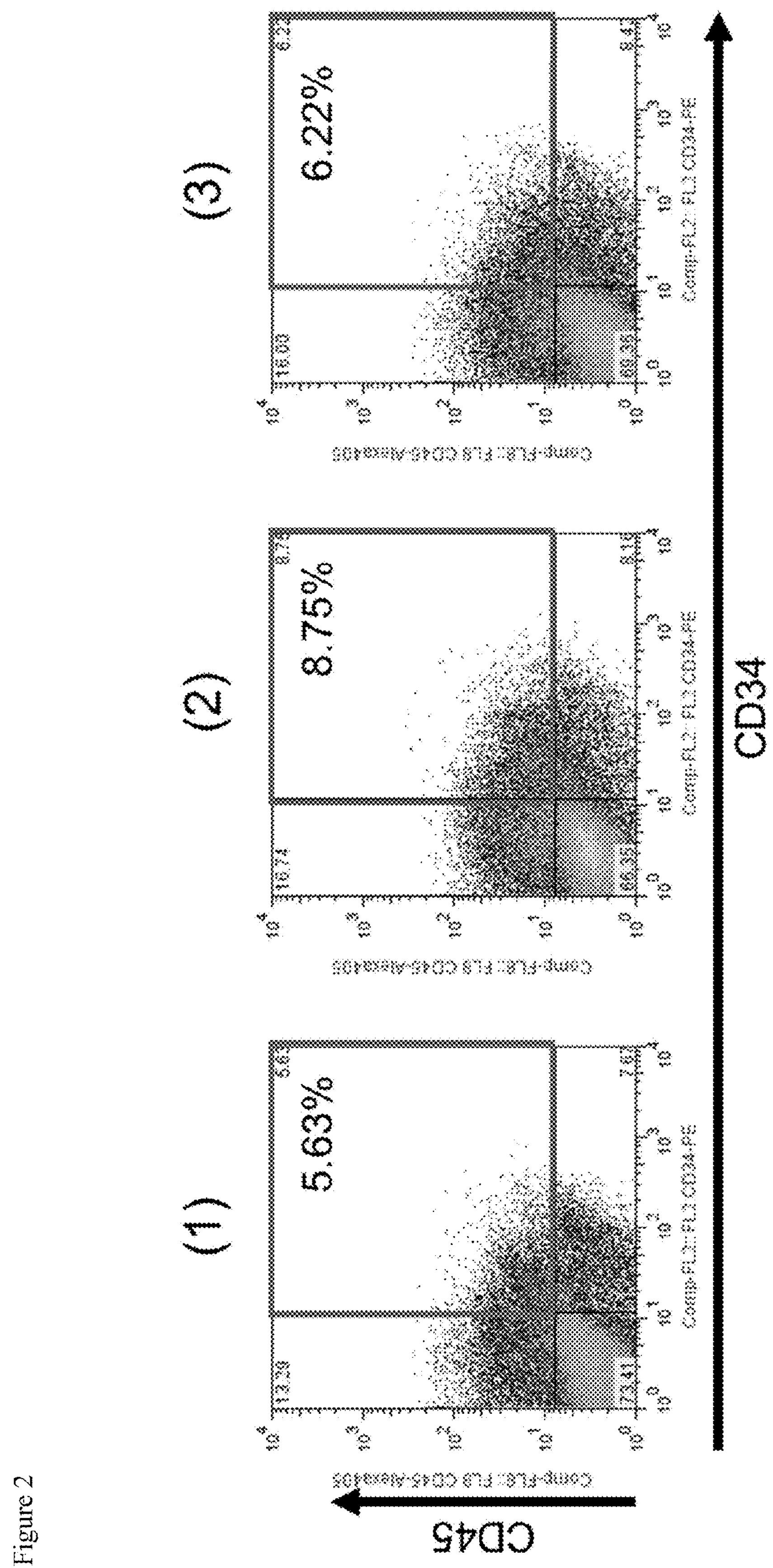
FIG. 2 shows the effects of a low oxygen culture on differentiation into hematopoietic progenitor cells (HPCs). The effects of a low oxygen culture on differentiation into HPCs were studied using flow cytometry. In the figure, (1) indicates the results of a culture performed under an oxygen partial pressure of 21% for 14 days; (2) indicates the results of a culture performed under an oxygen partial pressure of 5% for 7 days and then under an oxygen partial pressure of 21% for 7 days; and (3) indicates the results of a culture performed under an oxygen partial pressure of 5% for 14 days. In the experiments, iPS cells (cell line: TkCB7-4) were used.

The effects of a low oxygen culture on the differentiation of iPS cells into HPCs were studied. Human iPS cells were cultured under an atmospheric oxygen partial pressure (21%) for 14 days (FIG. 2 (1)); or human iPS cells were cultured under a low oxygen partial pressure (5%) for 7 days and then under an atmospheric oxygen partial pressure (21%) for 7 days (FIG. 2 (2)); or human iPS cells were cultured under a low oxygen partial pressure (5%) for 14 days (FIG. 2 (3)). The percentage of CD34-positive and CD45-positive cells used as markers for hematopoietic progenitor cells in the entire cells generated in an iPS-Sac was measured by flow cytometry in each of the three above cases. As a result, it was found that the percentage of hematopoietic progenitor cells is improved by culturing the iPS cells under a low oxygen partial pressure for a certain period of time (FIG. 2 (2)) (FIG. 2 (3)).

Subsequently, the effects of a low oxygen culture on the differentiation of iPS cells into hematopoietic progenitor cells were studied by performing colony assay of HPCs.

Figure 3:
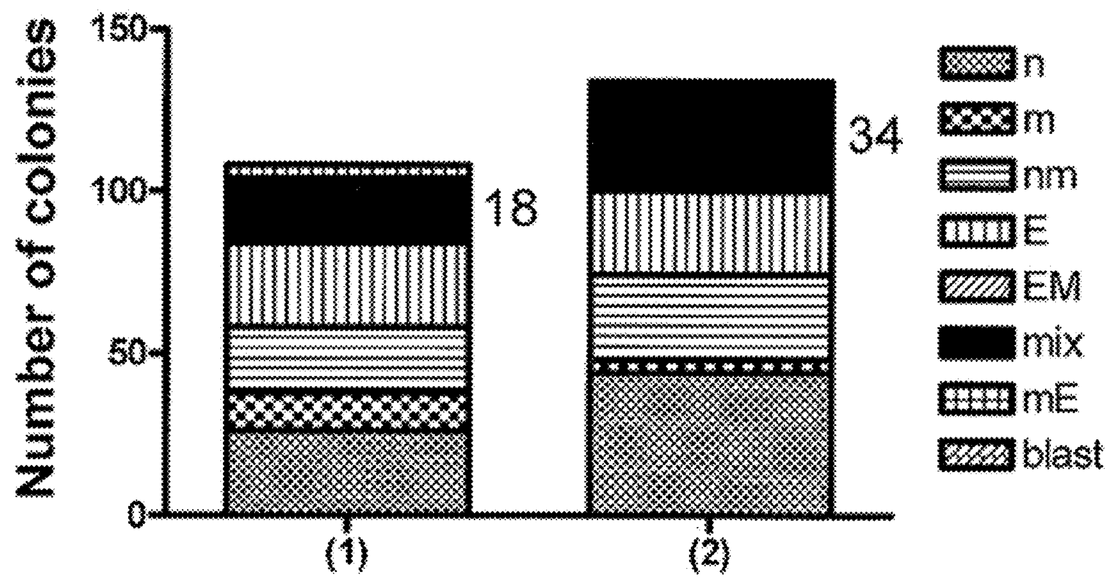
FIG. 3 shows the results obtained by studying the effects of a low oxygen culture on differentiation into hematopoietic progenitor cells by colony assay. In the figure, (1) indicates the results of a culture performed under an oxygen partial pressure of 21% for 14 days; and (2) indicates the results of a culture performed under an oxygen partial pressure of 5% for 7 days and then under an oxygen partial pressure of 21% for 7 days. The symbols “n,” “m,” “E,” “M” and “blast” indicate neutrophil, macrophage, erythroblast, megakaryocyte and hematopoietic blast cell, respectively. A combination of such letters means that the cells corresponding to individual letters are mixed (for example, “nm” means that neutrophils are present together with macrophages). The longitudinal axis indicates the number of colonies derived from $1\times10^4$ blood cells. The number that is close to each bar in the graph indicates the number of mixed colonies. In the experiments, iPS cells (cell line: TkCB7-2) were used.

Blood cells recovered from an iPS-Sac formed with iPS cells (TkCB7-2) were plated in a concentration of $1\times10^4$ on a medium, and the number of colonies generated after completion of a culture was then counted. The types of blood cells (n (neutrophils), m (macrophages), E (erythroblasts), M (megakaryocytes), and blast (hematopoietic blast cells)), which were present in each colony, were observed. As a result, it was found that the number of colonies formed in the case of culturing the iPS cells under a low oxygen partial pressure (5%) for 7 days and then under an atmospheric oxygen partial pressure (21%) for 7 days (FIG. 3 (2)) was larger than the number of colonies formed in the case of culturing the iPS cells under an atmospheric oxygen partial pressure (21%) for 14 days (FIG. 2 (1)). By the way, mixed colonies (mix) having all of the 4 types of blood cells act as indicators for the fact that they contain hematopoietic stem cells/hematopoietic progenitor cells. Such mixed colonies were formed in larger quantities in the case of culturing the cells under a low oxygen partial pressure than in the case of culturing the cells under an atmospheric oxygen partial pressure (FIG. 3; the number of mixed colonies was 18 in the culture under an atmospheric oxygen partial pressure, whereas it was 34 in the culture under a low oxygen partial pressure).

Figure 4:
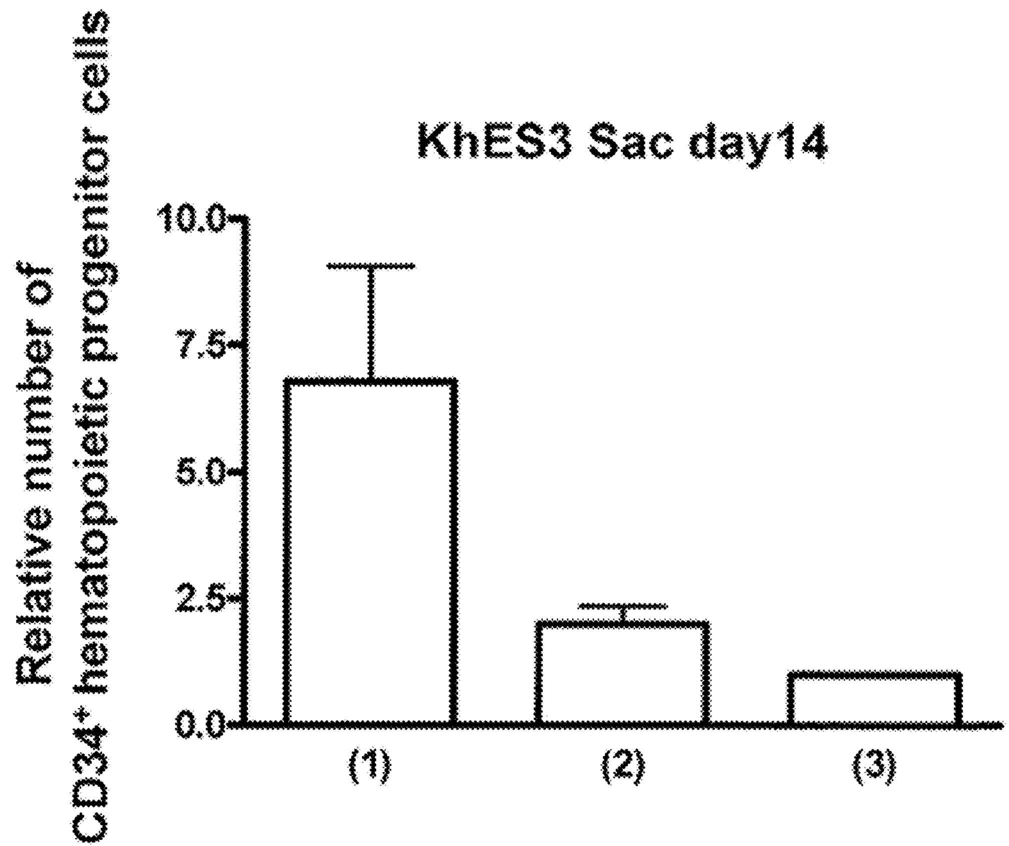
FIG. 4 shows the results obtained by evaluating the effects of a low oxygen culture on differentiation into hematopoietic progenitor cells by counting the number of CD34-positive cells. Herein, ES cells (cell line: KhES3) were used as pluripotent stem cells. In the figure, (1) indicates the results of a culture performed in the presence of VEGF, under an oxygen partial pressure of 5% for 7 days and then under an oxygen partial pressure of 21% for 7 days; (2) indicates the results of a culture performed in the presence of VEGF under an oxygen partial pressure of 21% for 14 days; and (3) indicates the results of a culture performed in the absence of VEGF under an oxygen partial pressure of 21% for 14 days. The longitudinal axis indicates the number of CD34-positive cells, when the number of CD34-positive cells obtained as a result of (3) above is defined as 1.

The effects of a low oxygen culture on the differentiation of ES cells (KhES3) into HPCs were also studied. ES cells were cultured under a low oxygen partial pressure (5%) for 7 days and then under an atmospheric oxygen partial pressure (21%) for 7 days (FIG. 4 (1)) (+VEGF); or ES cells were cultured under an atmospheric oxygen partial pressure (21%) for 14 days (+VEGF) (FIG. 4 (2)); or ES cells were cultured under an atmospheric oxygen partial pressure (21%) for 14 days (-VEGF) (FIG. 4 (3)). Thereafter, the number of CD34-positive cells generated in an ES-Sac was counted in each of the three above cases. As a result, it was found that the number of hematopoietic progenitor cells is increased by culturing the ES cells under a low oxygen partial pressure (a comparison made between FIG. 4 (1) and FIG. 4 (2); the longitudinal axis indicates a relative number, when the number of hematopoietic progenitor cells obtained by culturing ES cells under an atmospheric oxygen partial pressure (21%) for 14 days (-VEGF) is defined as 1).

From the above results, it became clear that, when pluripotent stem cells such as iPS cells or ES cells are differentiated into hematopoietic progenitor cells, the number of hematopoietic progenitor cells generated can be increased by including a step of culturing the pluripotent stem cells under a low oxygen partial pressure in the differentiation process.

Figure 5:
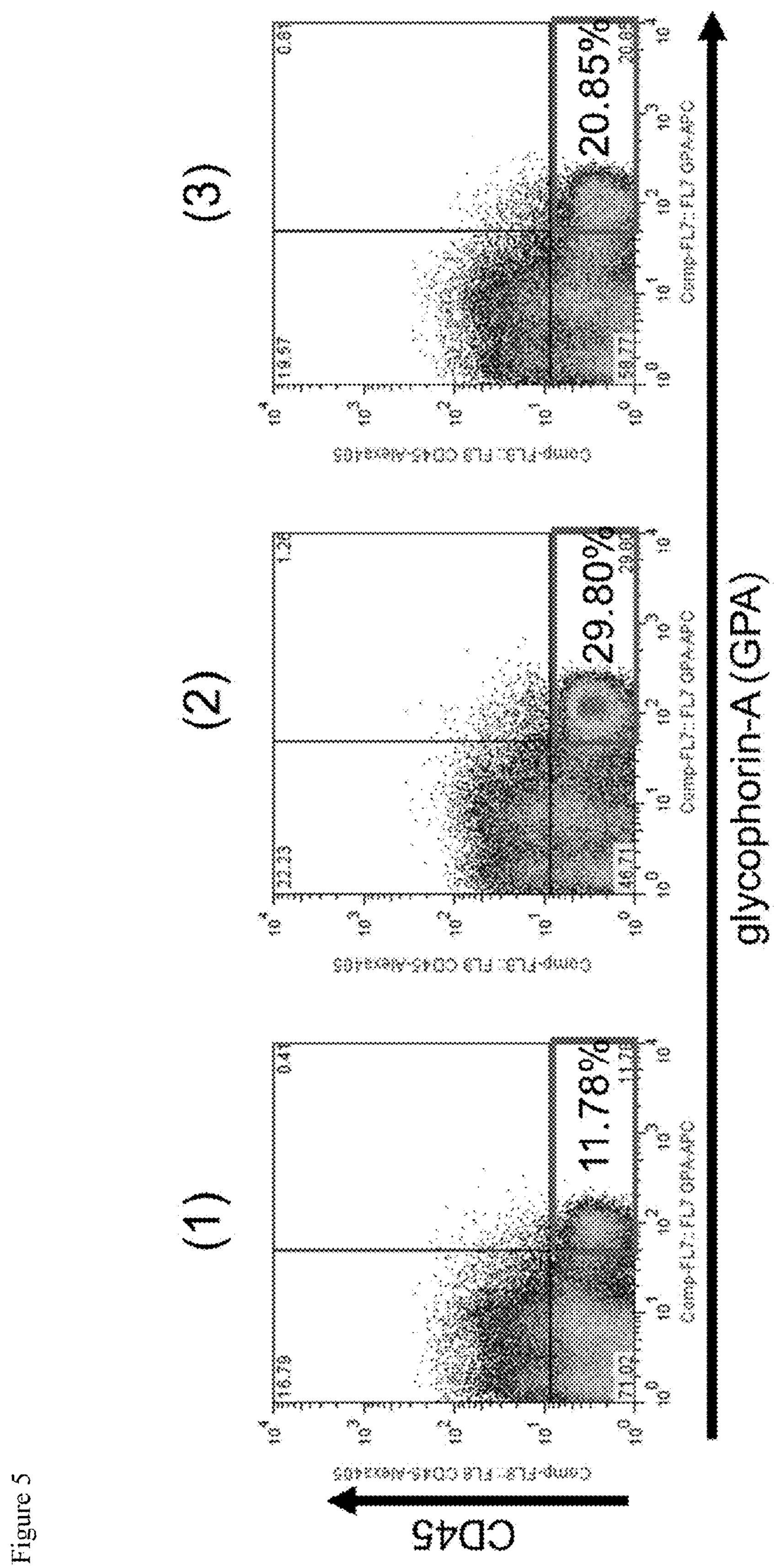
FIG. 5 shows the results obtained by studying the effects of a low oxygen culture on differentiation into erythroid cells, using flow cytometry. In the figure, (1) indicates the results of a culture performed under an oxygen partial pressure of 21% for 14 days; (2) indicates the results of a culture performed under an oxygen partial pressure of 5% for 7 days and then under an oxygen partial pressure of 21% for 7 days; and (3) indicates the results of a culture performed under an oxygen partial pressure of 5% for 14 days. The experiments (1), (2), and (3) were all carried out in the presence of 20 ng/ml VEGF. In the experiments, iPS cells (cell line: TkCB7-4) were used.

3. Effects of Low Oxygen Culture on Differentiation of iPS Cells into Erythroid Cells The effects of a low oxygen culture on the differentiation of iPS cells into erythroid progenitor cells were studied. Human iPS cells were cultured under an atmospheric oxygen partial pressure (21%) for 14 days (FIG. 5 (1)); or human iPS cells were cultured under a low oxygen partial pressure (5%) for 7 days and then under an atmospheric oxygen partial pressure (21%) for 7 days (FIG. 5 (2)); or human iPS cells were cultured under a low oxygen partial pressure (5%) for 14 days (FIG. 5 (3)). Thereafter, the percentage of GPA-positive and CD45-negative cells as markers for erythroid progenitor cells in the entire cells generated in an iPS-Sac was measured by flow cytometry in each of the three above cases. As a result, it was found that the percentage of erythroid progenitor cells becomes highest in the case of culturing the iPS cells under a low oxygen partial pressure for 7 days and then under an atmospheric oygen partial pressure for 7 days (FIG. 5 (2)).

Thus, it was demonstrated that a culture performed under a low oxygen partial pressure is effective even in the case of differentiating pluripotent stem cells into erythroid cells.

4. Effect of Low Oxygen Culture of Increasing Numbers of Various Types of Blood Cells HPCs, which had been produced by shifting the oxygen partial pressure from an oxygen partial pressure of 5% (a culture for 7 days) to an oxygen partial pressure of 21% (a culture for 7 days), was differentiated into mature erythrocytes, megakaryocytes, and platelets. Then, the effect of increasing the number of peripheral blood cells, caused by optimizing an oxygen partial pressure applied during the cell culture, was examined.

Figure 6:
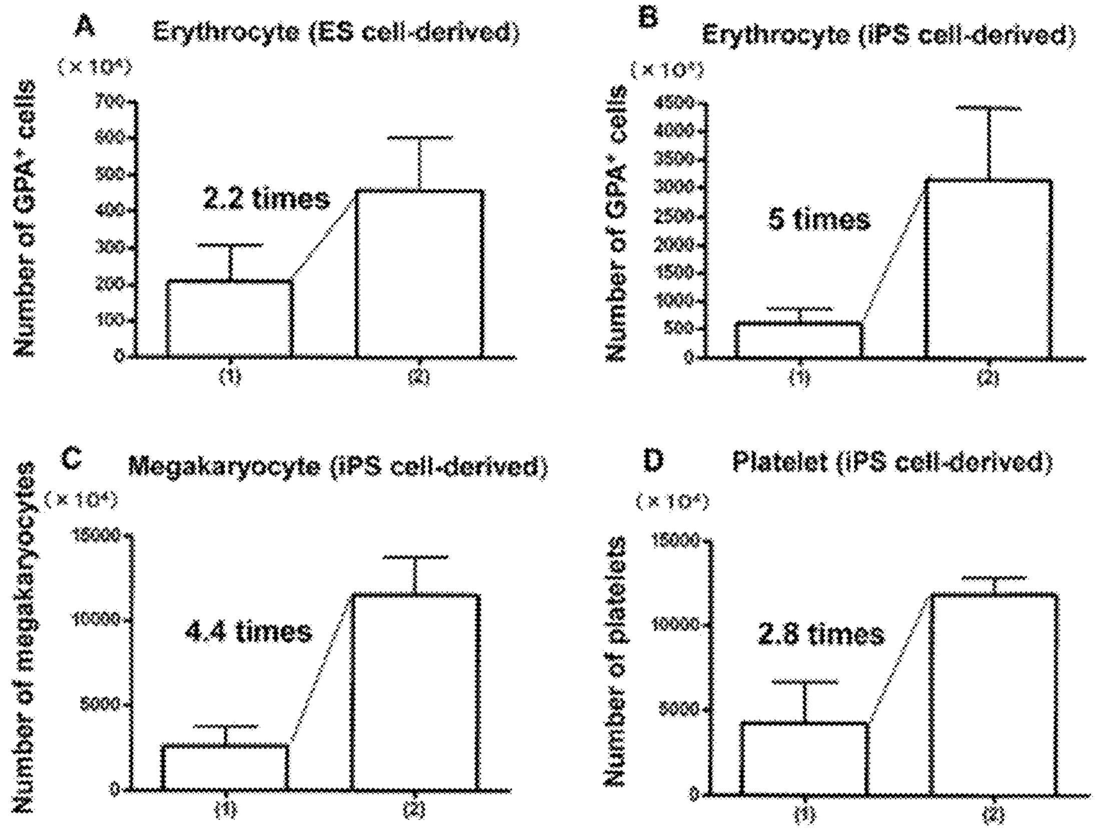
FIG. 6 shows the results obtained by examining the effects of a low oxygen culture on the numbers of various types of blood cells obtained from pluripotent stem cells.

As a result, the number of mature erythrocytes obtained by culturing $1\times10^5$ ES cells (KhES-3) under an oxygen partial pressure of 5% was approximately 2.2 times higher than the number of mature erythrocytes obtained by culturing the cells under an oxygen partial pressure of 21% (FIG. 6A). In the case of using iPS cells (TkCB7-2), the number of mature erythrocytes obtained by culturing under an oxygen partial pressure of 5% was approximately 5 times higher than the number of mature erythrocytes obtained by culturing the iPS cells under an oxygen partial pressure of 21% (FIG. 6B). Moreover, in the case of differentiation into megakaryocytes/platelets, the number of megakaryocytes obtained by culturing $1\times10^5$ iPS cells under an oxygen partial pressure of 5% was approximately 4.4 times higher than the number of megakaryocytes obtained by culturing the iPS cells under an oxygen partial pressure of 21% (FIG. 6C), and the number of platelets obtained by culturing $1\times10^5$ iPS cells under an oxygen partial pressure of 5% was approximately 2.8 times higher than the number of platelets obtained by culturing the iPS cells under an oxygen partial pressure of 21% (FIG. 6D). From these results, it was demonstrated that the present technique is effective for production of various types of blood cells from pluripotent stem cells.

5. Effects of Low Oxygen Culture on Percentage of β Globin-positive Cells in Erythrocytes HPCs, which had been produced by shifting the oxygen partial pressure from an oxygen partial pressure of 5% (a culture for 7 days) to an oxygen partial pressure of 21% (a culture for 7 days), was differentiated into mature erythrocytes, and the percentage of β globin-positive cells was then measured. β globin was used as an indicator for the maturity of erythrocytes.

Figure 7:
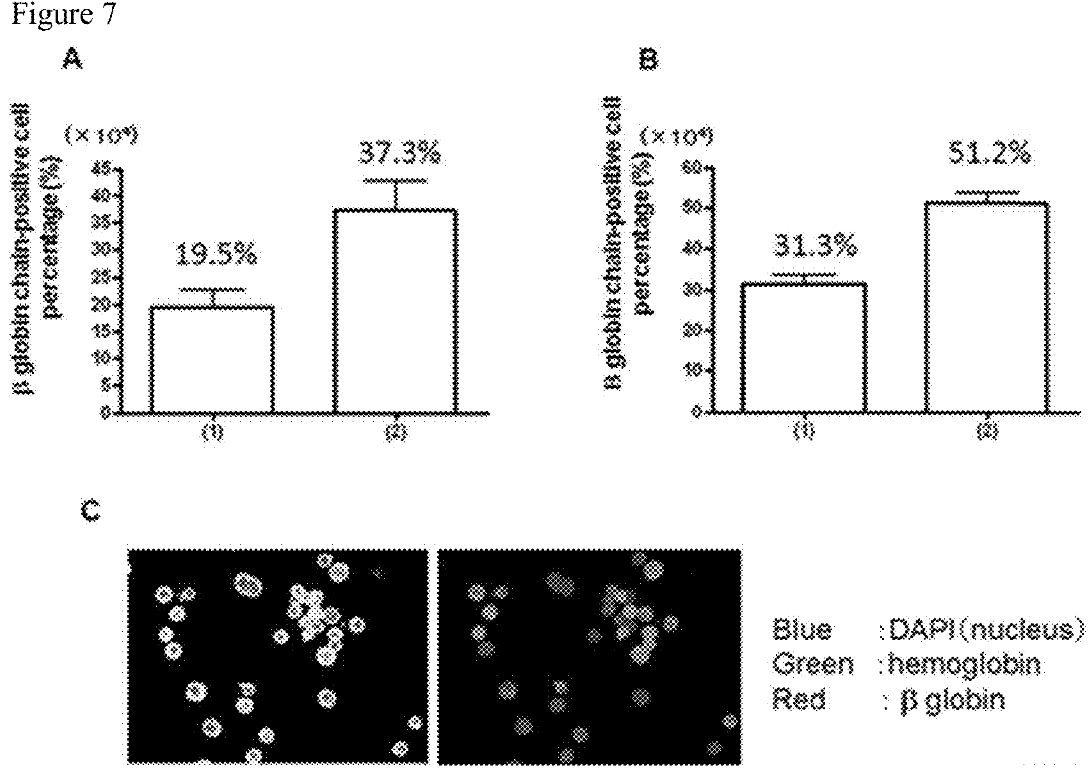
FIG. 7 shows the results obtained by studying the percentage of β globin-positive cells in the HPCs cultured under a low oxygen partial pressure.

As a result, the percentage of β globin-positive cells in erythrocytes obtained by the differentiation of HPC that had been produced from ES cells (KhES-3) under an oxygen partial pressure of 21% was 19.5% (FIG. 7A (1)), whereas the percentage of β globin-positive cells in erythrocytes obtained by the differentiation of HPCs that had been produced from ES cells (KhES-3) while shifting the oxygen partial pressure from an oxygen partial pressure of 5% to an oxygen partial pressure of 21% was 37.3% (FIG. 7A (2)). Thus, the maturity of erythrocytes was improved. Likewise, the percentage of β globin-positive cells in erythrocytes obtained by the differentiation of HPCs that had been produced from iPS cells (TkCB7-2) under an oxygen partial pressure of 21% was 31.3% (FIG. 7B (1)), whereas the percentage of β globin-positive cells in erythrocytes obtained by the differentiation of HPCs that had been produced from iPS cells (TkCB7-2) while shifting the oxygen partial pressure from an oxygen partial pressure of 5% to an oxygen partial pressure of 21% was 51.2% (FIG. 7B (2)).

From the above results, it was found that peripheral blood cells having high maturity can be produced by the present technique.

6. Studies Regarding Substitution of Low Oxygen Culture for VEGF

Figure 8:
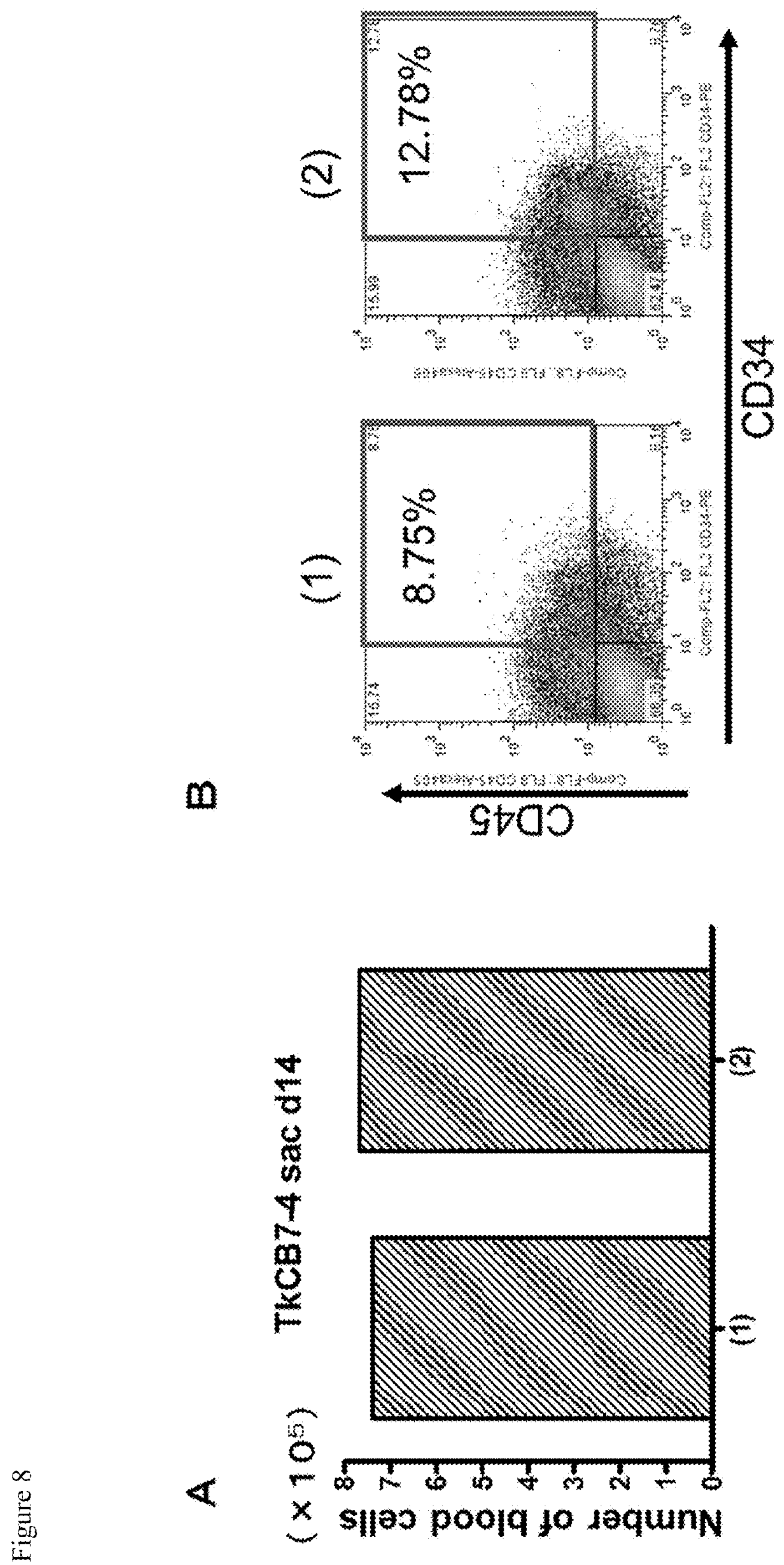
FIG. 8 shows the results obtained by studying the substitution of a low oxygen culture for VEGF.

In order to efficiently differentiate pluripotent stem cells into blood cells via the formation of a sac-like structure, an addition of VEGF is desirable. Hence, the possibility of a low oxygen culture that can substitute for the effect of VEGF was examined.

iPS cells (TkCB7-4) were cultured in the presence of VEGF for 14 days under an atmospheric oxygen partial pressure (21%) (FIG. 8A (1)). On the other hand, the iPS cells were cultured in the absence of VEGF for 7 days under a low oxygen partial pressure (5%) and then for 7 days under an atmospheric oxygen partial pressure (21%) (FIG. 8A (2)). In both of the two cases, the number of blood cells generated in an iPS-Sac was counted. As a result, the number of blood cells generated was slightly higher in the case of culturing the cells under a low oxygen partial pressure without adding VEGF than in the case of culturing the cells under an atmospheric oxygen partial pressure with an addition of VEGF.

Subsequently, the percentage of CD34-positive and CD45-positive cells as markers for hematopoietic progenitor cells in the cells generated in the iPS-Sac was measured by flow cytometry. As a result, the percentage of the hematopoietic progenitor cells was slightly higher in the case of culturing the cells under a low oxygen partial pressure without adding VEGF than in the case of culturing the cells under an atmospheric oxygen partial pressure with an addition of VEGF (FIG. 8B).

Moreover, the substitution of a low oxygen culture for VEGF was examined by colony assay. Blood cells recovered from iPS cells (TkCB7-4 (FIG. 9A) and TkCB8-3 (FIG. 9B)) were plated in a concentration of $5\times10^3$ (TkCB7-4 (FIG. 9A)) or $1\times10^4$ (TkCB8-3 (FIG. 9B)) on a medium, and thereafter, colony assay was carried out. As a result, the number of colonies formed was higher in the case of culturing the cells in the absence of VEGF under a low oxygen partial pressure (5%) for 7 days and then under an atmospheric oxygen partial pressure (21%) for 7 days (FIGS. 9A (2) and 9B (2)) than in the case of culturing the cells in the presence of VEGF under an atmospheric oxygen partial pressure (21%) (FIGS. 9A (1) and B (1)). In addition, the number of mixed colonies was also increased in the former case.

Figure 9:
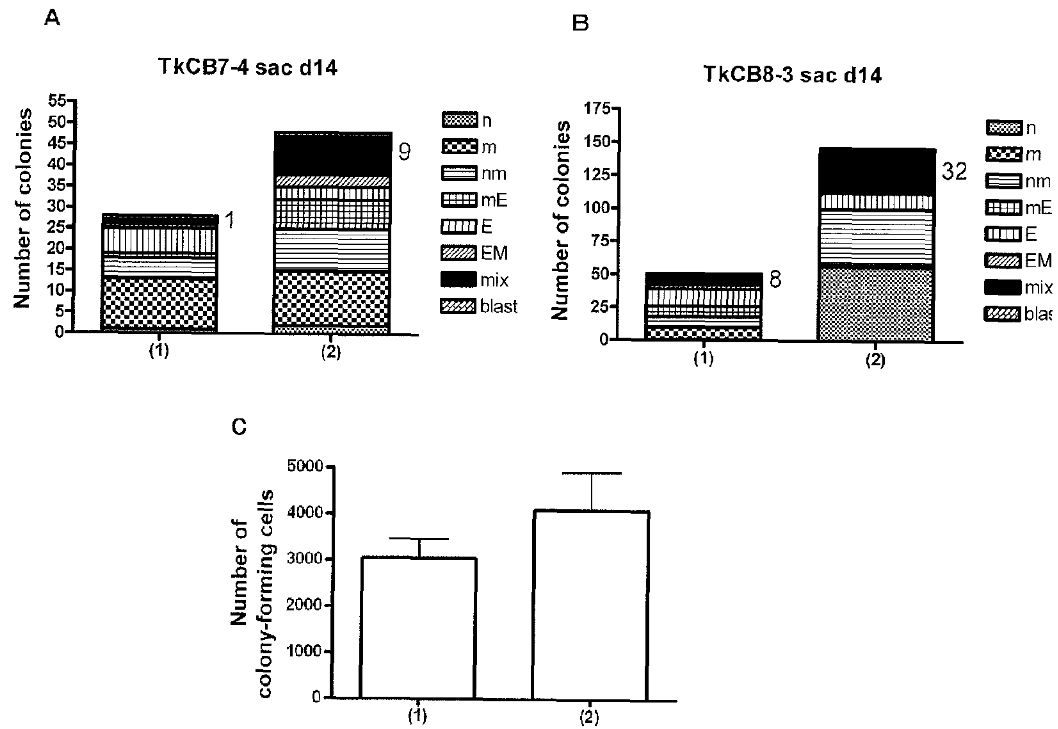
FIG. 9 shows the results obtained by examining the substitution of a low oxygen culture for VEGF by colony assay.

Furthermore, the number of colonies formed in blood cells obtained by culturing ES cells in the presence of VEGF, while shifting the oxygen partial pressure from 5% to 21%, tended to be increased in comparison with the case of culturing the cells in the absence of VEGF (FIG. 9C).

These results demonstrated that a low oxygen culture can be substituted for the effects of VEGF, and also that a combination of such a low oxygen culture and VEGF can increase the number of hematopoietic progenitor cells generated and can produce hematopoietic progenitor cells having a high potential to differentiate into blood.

7. Effects of Culture Performed Under Oxygen Partial Pressure of 1%

Figure 10:
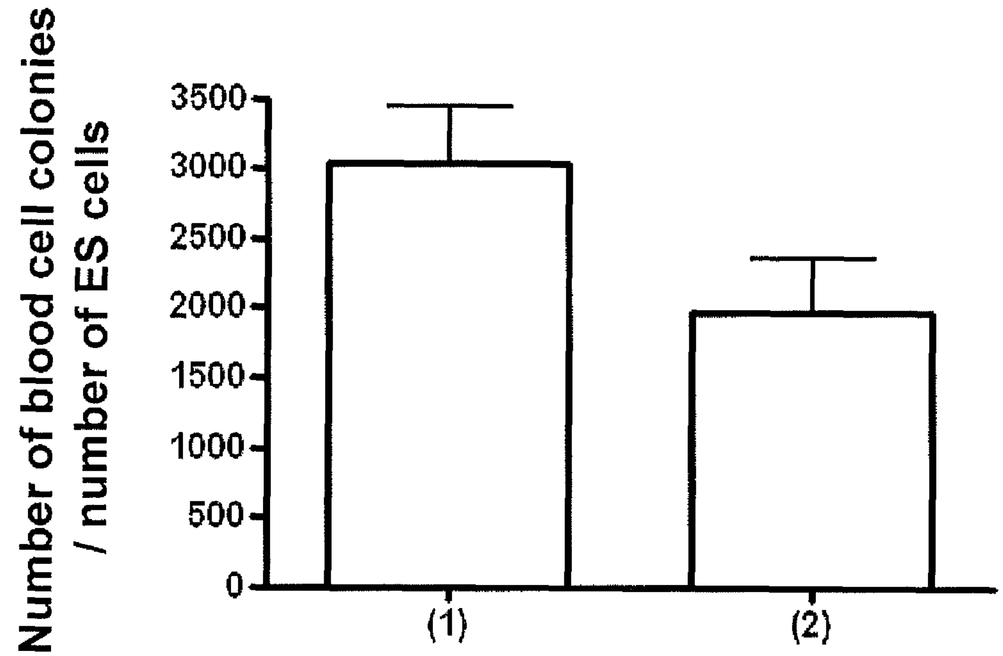
FIG. 10 shows the results obtained by studying the effects of a culture performed under an oxygen partial pressure of 1%. In the figure, (1) indicates the results of a culture performed in the absence of VEGF under an oxygen partial pressure of 5% for 7 days and then under an oxygen partial pressure of 21% for 7 days, and (2) indicates the results of a culture performed in the absence of VEGF under an oxygen partial pressure of 1% for 7 days and then under an oxygen partial pressure of 21% for 7 days. The longitudinal axis indicates the number of blood cell colonies per number of ES cells ($1\times10^5$) at the beginning of the culture. In the experiments, ES cells (cell line: KhES3) were used.

ES cells were cultured in the absence of VEGF under a low oxygen partial pressure (5%) for 7 days and then under an atmospheric oxygen partial pressure (21%) for 7 days (FIG. 10 (1)). On the other hand, ES cells were cultured under a lower oxygen partial pressure (1%) for 7 days and then under an atmospheric oxygen partial pressure (21%) for 7 days (FIG. 10 (2)). The two above cases were compared with each other, in terms of the number of blood cell colonies formed from the same number of ES cells. As a result, a larger number of blood cell colonies were formed in the case of culturing the ES cells under an oxygen partial pressure of 5%, and a number of hematopoietic progenitor cells could be obtained.

Figure 11:
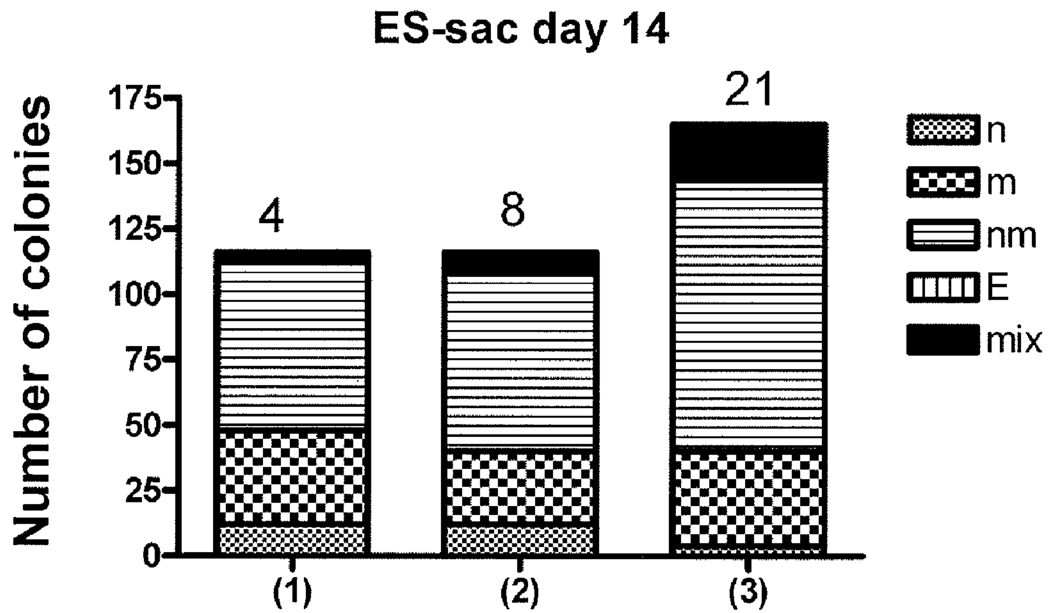
FIG. 11 shows the results obtained by studying the effects of a culture performed under an oxygen partial pressure of 1%. The figure shows the results obtained by carrying out colony assay on hematopoietic progenitor cells, which had been generated in each of the case (1) of performing a culture in the presence of VEGF under an oxygen partial pressure of 21% for 14 days, in the case (2) of performing a culture in the absence of VEGF under an oxygen partial pressure of 5% for 7 days and then under an oxygen partial pressure of 21% for 7 days, and in the case (3) of performing a culture in the absence of VEGF under an oxygen partial pressure of 1% for 7 days and then under an oxygen partial pressure of 21% for 7 days. The symbols "n," "m," "E," "M" and "blast" indicate neutrophil, macrophage, erythroblast, megakaryocyte and blast blood cell, respectively. A combination of such letters means that the cells corresponding to individual letters are mixed. The longitudinal axis indicates the number of blood cell colonies per number of ES cells ($1\times10^5$) at the beginning of the culture. The number that is close to each bar in the graph indicates the number of mixed colonies. In the experiments, ES cells (cell line. KhES3) were used.

Next, the ability of hematopoietic progenitor cells, which were generated by subjecting ES cells to a low oxygen partial pressure (1%), to differentiate into blood cells was studied using the number of mixed colonies generated as an indicator. ES cells were cultured in the presence of VEGF under an atmospheric oxygen partial pressure (21%) for 14 days (FIG. 11 (1)); or ES cells were cultured in the absence of VEGF under a low oxygen partial pressure (5%) for 7 days and then under an atmospheric oxygen partial pressure (21%) for 7 days (FIG. 11 (2)); or ES cells were cultured in the absence of VEGF under a low oxygen partial pressure (1%) for 7 days and then under an atmospheric oxygen partial pressure (21%) for 7 days (FIG. 11 (3)). The same number of $CD34^+$ cells were recovered from each of the three above cases, and the recovered cells were then subjected to colony assay. As a result, the number of colonies generated was highest in the case in which the culture was initiated under an oxygen partial pressure of 1%, and the number of mixed colonies generated was also highest (which was approximately 5 times higher than in the case of culturing the cells under an atmospheric oxygen partial pressure for the entire period, and which was approximately 2.6 times higher than in the case of beginning the culture under an oxygen partial pressure of 5%). From these results, it was found that, if a cell culture is initiated under a lower oxygen partial pressure (for example, approximately 1%), hematopoietic progenitor cells having a higher potential to differentiate into blood cells can be produced.

Figure 12:
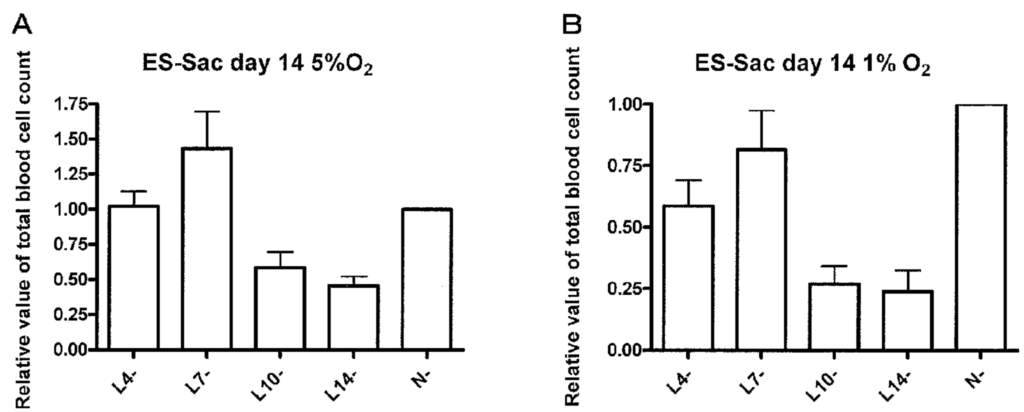
FIG. 12 shows the results obtained by studying the timing of shifting the culture condition from a culture performed under a low oxygen partial pressure to a culture performed under a higher oxygen partial pressure.

8. Studies Regarding Timing of Shifting Oxygen Environment from Low Oxygen Environment to Atmospheric Oxygen Environment ES cells (cell line: KhES3) were cultured under a low oxygen partial pressure (5% (FIG. 12A) or 1% (FIG. 12B)) for 4, 7, or 10 days, and they were then cultured under an atmospheric oxygen partial pressure for the remaining period. Or, the ES cells were cultured under a low oxygen partial pressure for the entire period (14 days). Otherwise, the ES cells were cultured under an atmospheric oxygen partial pressure for the entire period (14 days). In each of these three cases, the number of blood cells generated after completion of the culture was counted. As a result, it was found that the number of blood cells generated was highest in the case of culturing the ES cells under a low oxygen partial pressure for a culture period of 7 days, and further that as the culture period under a low oxygen partial pressure is prolonged, the efficiency of forming blood cells decreases (L7 in each of FIGS. 12A and 12B). Accordingly, if the oxygen partial pressure condition during the culture were shifted from a low oxygen partial pressure to an atmospheric oxygen partial pressure around Day 7 of the culture, the ES cells could be differentiated into blood cells most efficiently. It would be desirable to shift the oxygen partial pressure condition during the culture, at the latest Day 10 of the culture, from a low oxygen partial pressure to an atmospheric oxygen partial pressure.

9. Studies Regarding Change in Gene Expression Under Culture Conditions Comprising Low Oxygen Partial Pressure ES cells (KhES-3) were cultured under a low oxygen partial pressure (5%) for 14 days (5% L14). On the other hand, the ES cells were cultured under a low oxygen partial pressure (5%) for 7 days and then under an atmospheric oxygen partial pressure (21%) (5% L7). A change in gene expression in each case was analyzed by real-time PCR.

Figure 13:
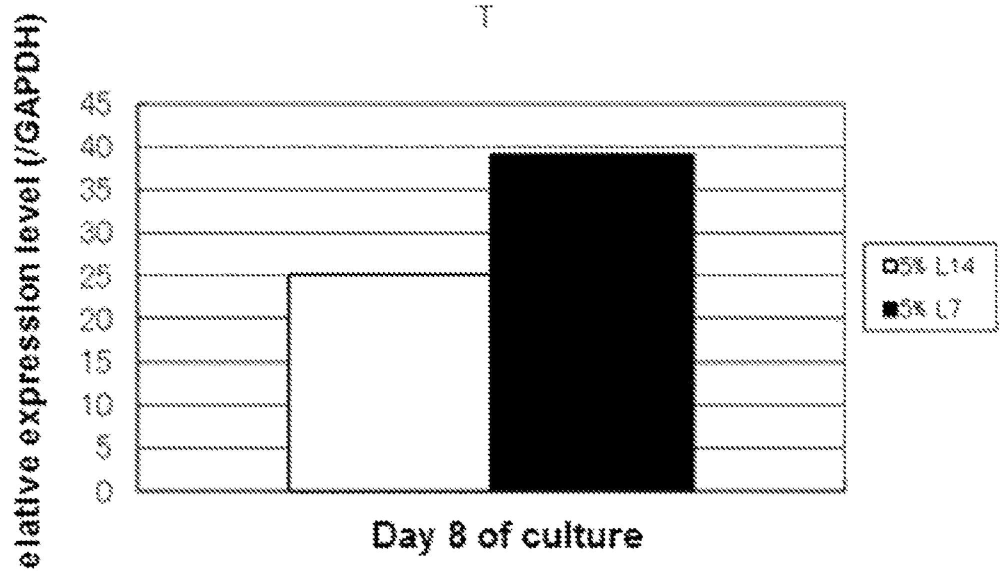
FIG. 13 shows the results obtained by studying a change in the expression of a gene (T) used as an indicator of mesendoderm induction, which is associated with a change in oxygen partial pressure. The longitudinal axis indicates the relative expression level of GAPDH. In addition, L7 indicates a case in which the applied pressure was shifted from a low oxygen partial pressure (an oxygen partial pressure of 5%) to an atmospheric oxygen partial pressure (an oxygen partial pressure of 21%) on the $7^{th}$ day after the beginning of the culture. L14 indicates a case in which the culture was entirely carried out under a low oxygen partial pressure (an oxygen partial pressure of 5%). The gene expression was examined on the $8^{th}$ day of the culture.

When compared with 5% L14, the expression level of a gene used as an indicator of mesendoderm induction (for example, T) (FIG. 13) was increased on Day 8 of the culture in the case of 5% L7. Thereafter, the expression of the T gene was gradually decreased after Day 8 of the culture, regardless of oxygen partial pressure.

Figure 14:
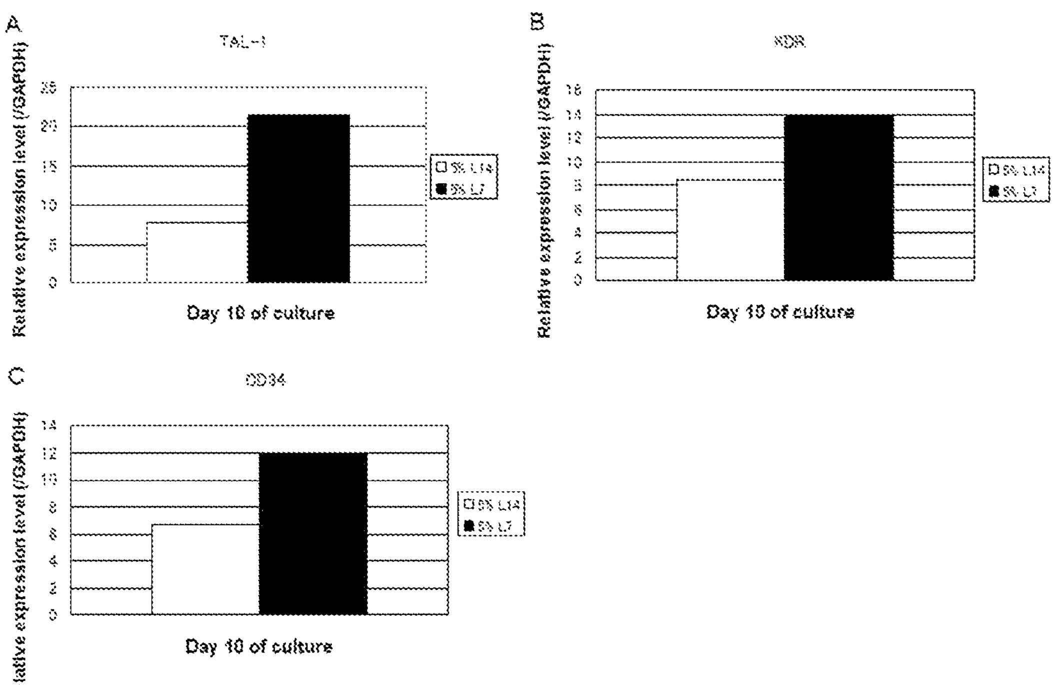
FIG. 14 shows the results obtained by studying a change in the expression of genes (TAL-1 (A), KDR (B), and CD34 (C)) used as indicators of hematopoietic progenitor cell induction, which is associated with a change in oxygen partial pressure. The longitudinal axis indicates the relative expression level of GAPDH. L7 and L14 have the same definitions as those described in FIG. 13. The gene expression was examined on the $10^{th}$ day of the culture.
Figure 15:
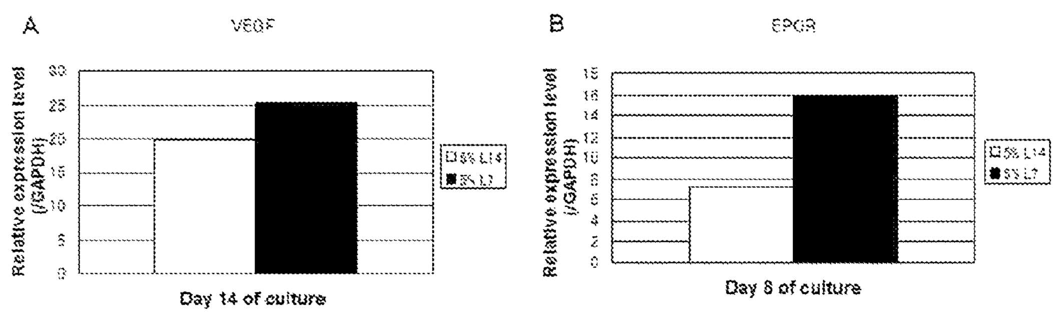
FIG. 15 shows the results obtained by studying a change in the expression of genes used as indicators of cytokine (VEGF (A) and EPOR (B)), which is associated with a change in oxygen partial pressure. The longitudinal axis indicates the relative expression level of GAPDH. L7 and L14 have the same definitions as those described in FIG. 13. The expression of VEGF was examined on the $14^{th}$ day of the culture, and the expression of EPOR was examined on $8^{th}$ day of the culture.
Figure 16:
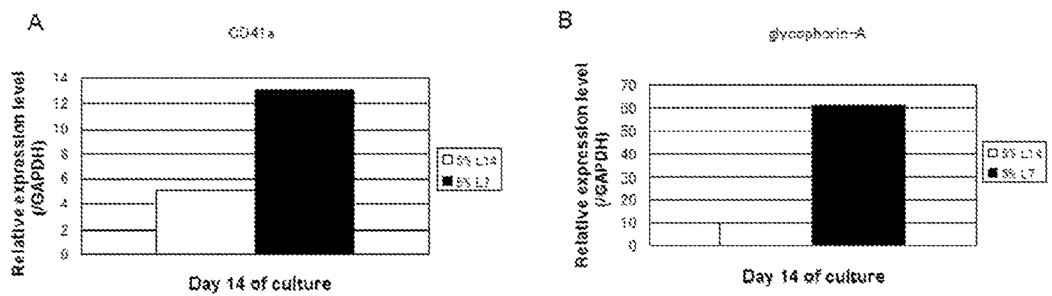
FIG. 16 shows the results obtained by studying a change in the expression of genes (CD41a (A) and Glycophorin-A (B)) used as indicators of blood cell induction, which is associated with a change in oxygen partial pressure. The longitudinal axis indicates the expression of each gene relative to the expression of GAPDH. L7 and L14 have the same definitions as those described in FIG. 13. The gene expression was examined on the $14^{th}$ day of the culture.

Moreover, after Day 8 of the culture, the expression levels of genes used as indicators of hematopoietic progenitor cell induction (for example, TAL-1 (FIG. 14A), KDR (FIG. 14B), and CD34 (FIG. 14C)), genes used as indicators of cytokine (for example, VEGF (FIG. 15A) and EPOR (FIG. 15B)), and genes used as indicators of blood cell induction (for example, CD41a (FIG. 16A) and Glycophorin-A (FIG. 16B)) were increased. The expression levels of these genes were continuously increased until Day 14 of the culture, and 5% L7 consistently exhibited high expression tendency.

Figure 17:
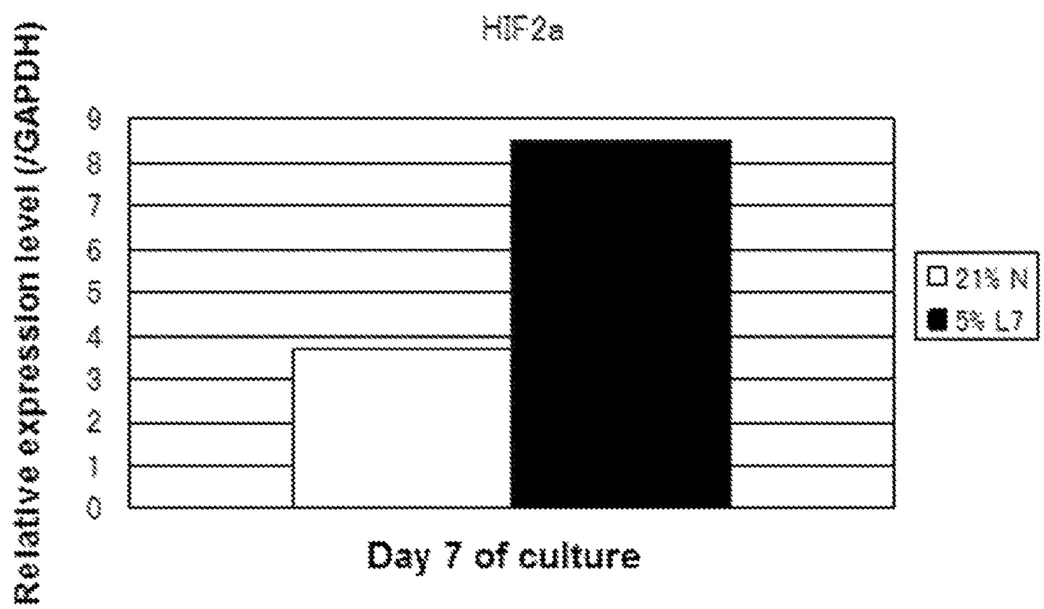
FIG. 17 shows the results obtained by studying a change in the expression of a hypoxia-responsive gene (HIF2a), which is associated with a change in oxygen partial pressure. The longitudinal axis indicates the expression of the gene relative to the expression of GAPDH. In addition, N- indicates a case in which a culture was entirely performed under an oxygen partial pressure of 21%, and L7 has the same definition as that in FIG. 13. The gene expression was examined on the $7^{th}$ day of the culture.

In addition, on Day 7 of the culture, before the oxygen partial pressure was changed, the atmospheric oxygen (21% N) was compared with the low oxygen (5% L7). As a result, it was found that the expression levels of hypoxia-responsive genes (for example, HIF2α) were increased (FIG. 17).

From these results, it was found that the expression levels of these genes are changed with oxygen partial pressure, and thus that they can be used as indicators for determining the timing of shifting the oxygen partial pressure or the concentration of oxygen partial in the gas that is applied.

Industrial Applicability

The present invention provides a method for efficiently differentiating blood cells in vitro. Since it becomes possible to easily supply sufficient amounts of blood cells in vitro according to the present invention, the present invention greatly contributes to the development of a medical field and the like.

The invention claimed is:

1. A method for producing hematopoietic progenitor cells or erythroid progenitor cells, which comprises culturing cells selected from the group consisting of pluripotent stem cells and cells at a differentiation stage between pluripotent stem cells and hematopoietic progenitor cells, and increasing an oxygen partial pressure from a low oxygen partial pressure of up to 10% to a higher oxygen partial pressure of at least 11% during said culturing of said cells, thereby producing the hematopoietic progenitor cells or the erythroid progenitor cells, wherein the low oxygen partial pressure is increased to the higher oxygen partial pressure when an indicator gene is expressed that indicates expression of a differentiation induction and the gene is selected from the group consisting of mesendoderm induction, hematopoietic progenitor cell induction, differential proliferative cytokine, and blood cell induction.

2. The method for producing hematopoietic progenitor cells or erythroid progenitor cells according to claim 1, wherein the low oxygen partial pressure is 0.1% to 10%.

3. The method for producing hematopoietic progenitor cells or erythroid progenitor cells according to claim 1, wherein the low oxygen partial pressure is an oxygen partial pressure at which a hypoxia-responsive gene is expressed at a higher level than that in a case in which the cells are cultured under other partial pressures.

4. The method for producing hematopoietic progenitor cells or erythroid progenitor cells according to claim 1, wherein the cells are cultured under the low oxygen partial pressure for a certain period of time after the beginning of the cell culture, and thereafter, the cells are further cultured under said higher oxygen partial pressure, wherein the certain period of time coincides with when an indicator gene is expressed and the time period is for 4 to 10 days.

5. The method for producing hematopoietic progenitor cells or erythroid progenitor cells according to claim 1, wherein the higher oxygen partial pressure is an oxygen partial pressure of 11% to 30%.

6. The method for producing hematopoietic progenitor cells or erythroid progenitor cells according to claim 1, wherein the cells capable of differentiating into hematopoietic progenitor cells or erythroid progenitor cells are pluripotent stem cells.

7. The method for producing hematopoietic progenitor cells or erythroid progenitor cells according to claim 1, wherein after said increasing of said oxygen partial pressure said culturing is carried out in an environment that forms a sac-like structure or an embryoid; and obtaining the hematopoietic progenitor cells or the erythroid progenitor cells from said sac-like structure or said embryoid.

8. The method for producing hematopoietic progenitor cells or erythroid progenitor cells according to claim 1, which is characterized in that VEGF is not added to a medium in which the cell culture is carried out.

9. A method comprising carrying out a first said production method according to claim 1 to produce said hematopoietic progenitor cells and optionally said erythroid progenitor cells; carrying out a second said production method according to claim 1 while adding to said culture a candidate substance to produce said hematopoietic progenitor cells and optionally said erythroid progenitor cells; and comparing results of said first method and said second method to evaluate whether said candidate substance promotes or inhibits differentiation into said hematopoietic progenitor cells or said erythroid progenitor cells.

10. A method comprising culturing the hematopoietic progenitor cells or erythroid progenitor cells produced according to the method of claim 1 to produce blood cells.

11. The method for producing hematopoietic progenitor cells or erythroid progenitor cells according to claim 1 wherein said higher oxygen partial pressure is atmospheric oxygen partial pressure.

12. The method for producing hematopoietic progenitor cells or erythroid progenitor cells according to claim 1, wherein the expressed indicator gene is KDR+, CD34+ or CD43+.

13. A method for producing hematopoietic progenitor cells or erythroid progenitor cells, which comprises culturing cells selected from the group consisting of pluripotent stem cells and cells at a differentiation stage between pluripotent stem cells and hematopoietic progenitor cells, and increasing an oxygen partial pressure from a low oxygen partial pressure of up to 10% to a higher oxygen partial pressure of at least 11% during said culturing of said cells, thereby producing the hematopoietic progenitor cells or the erythroid progenitor cells, wherein the cells are cultured under the low oxygen partial pressure for a certain period of time after the beginning of the cell culture, and thereafter, the cells are further cultured under said higher oxygen partial pressure, wherein the certain period of time is a period of time until $KDR^+$, $CD34^+$or $CD43^+$cells appear.

14. The method for producing hematopoietic progenitor cells or erythroid progenitor cells according to claim 13, wherein the higher oxygen partial pressure is an oxygen partial pressure of 11% to 30%.

15. The method for producing hematopoietic progenitor cells or erythroid progenitor cells according to claim 14 wherein said higher oxygen partial pressure is atmospheric oxygen partial pressure.

16. The method for producing hematopoietic progenitor cells or erythroid progenitor cells according to claim 13, wherein the low oxygen partial pressure is 0.1% to 10%.

17. The method for producing hematopoietic progenitor cells or erythroid progenitor cells according to claim 13, wherein after said increasing of said oxygen partial pressure said culturing is carried out in an environment that forms a sac-like structure or an embryoid; and obtaining the hematopoietic progenitor cells or the erythroid progenitor cells from said sac-like structure or said embryoid.

18. A method comprising culturing the hematopoietic progenitor cells or erythroid progenitor cells produced according to the method of claim 13 to produce blood cells.

19. The method for producing hematopoietic progenitor cells or erythroid progenitor cells according to claim 13, which is characterized in that VEGF is not added to a medium in which the cell culture is carried out.

20. A method for producing hematopoietic progenitor cells or erythroid progenitor cells, which comprises culturing cells selected from the group consisting of pluripotent stem cells and cells at a differentiation stage between pluripotent stem cells and hematopoietic progenitor cells, and increasing an oxygen partial pressure from a low oxygen partial pressure of up to 10% to a higher oxygen partial pressure of at least 11% during said culturing of said cells, thereby producing the hematopoietic progenitor cells or the erythroid progenitor cells, wherein the cells are cultured under the low oxygen partial pressure for a certain period of time after the beginning of the cell culture, and thereafter, the cells are further cultured under said higher oxygen partial pressure, which is characterized in that the time at which the low oxygen partial pressure is changed to said higher oxygen partial pressure is selected from the group consisting of: the time at which a gene used as an indicator of mesendoderm induction is expressed, the time at which the expression of a gene used as an indicator of hematopoietic progenitor cell induction begins, the time at which the expression of a gene used as an indicator of differential proliferative cytokine begins, and the time at which the expression of a gene used as an indicator of blood cell induction begins.

21. The method for producing hematopoietic progenitor cells or erythroid progenitor cells according to claim 20, wherein the higher oxygen partial pressure is an oxygen partial pressure of 11% to 30%.

22. The method for producing hematopoietic progenitor cells or erythroid progenitor cells according to claim 21 wherein said higher oxygen partial pressure is atmospheric oxygen partial pressure.

23. The method for producing hematopoietic progenitor cells or erythroid progenitor cells according to claim 20, wherein the low oxygen partial pressure is 0.1% to 10%.

24. The method for producing hematopoietic progenitor cells or erythroid progenitor cells according to claim 20, wherein after said increasing of said oxygen partial pressure said culturing is carried out in an environment that forms a sac-like structure or an embryoid; and obtaining the hematopoietic progenitor cells or the erythroid progenitor cells from said sac-like structure or said embryoid.

25. A method comprising culturing the hematopoietic progenitor cells or erythroid progenitor cells produced according to the method of claim 20 to produce blood cells.

26. The method for producing hematopoietic progenitor cells or erythroid progenitor cells according to claim 20, which is characterized in that VEGF is not added to a medium in which the cell culture is carried out.

27. A method for producing hematopoietic progenitor cells, comprising:

culturing cells selected from the group consisting of pluripotent stem cells and cells at a differentiation stage between pluripotent stem cells and hematopoietic progenitor cells;

increasing an oxygen partial pressure from a low oxygen partial pressure of 0.1% to 10% to a higher oxygen partial pressure of 11% to 30% during said culturing of said cells, thereby producing the hematopoietic progenitor cells;

wherein the cells are cultured under the low oxygen partial pressure for a certain period of time after the beginning of the cell culture, and thereafter, the cells are further cultured under said higher oxygen partial pressure;

wherein the time at which the low oxygen partial pressure is changed to said higher oxygen partial pressure is determined based on a time selected from the group consisting of: the time at which a gene used as an indicator of mesendoderm induction is expressed, the time at which the expression of a gene used as an indicator of hematopoietic progenitor cell induction begins, the time at which the expression of a gene used as an indicator of differential proliferative cytokine begins, and the time at which the expression of a gene used as an indicator of blood cell induction begins.

28. The method for producing hematopoietic progenitor cells according to claim 27 wherein said higher oxygen partial pressure is atmospheric oxygen partial pressure.

29. The method for producing hematopoietic progenitor cells according to claim 27, which is characterized in that VEGF is not added to a medium in which the cell culture is carried out.

* * * * *

UNITED STATES PATENT AND TRADEMARK OFFICE
CERTIFICATE OF CORRECTION

PATENT NO. : 8,778,681 B2
APPLICATION NO. : 13/790307
DATED : July 15, 2014
INVENTOR(S) : Shinya Sano et al.

It is certified that error appears in the above-identified patent and that said Letters Patent is hereby corrected as shown below:

In the Specification

In column 10, line 61, please delete “HIFα” and insert --HIF2α--

In column 12, line 40, please delete “IL-α” and insert --IL-1α--

Signed and Sealed this
Twenty-first Day of October, 2014

Michelle K. Lee

Michelle K. Lee
*Deputy Director of the United States Patent and Trademark Office*